US009715811B2

(12) United States Patent
Moriai

(10) Patent No.: US 9,715,811 B2
(45) Date of Patent: Jul. 25, 2017

(54) ELECTRONIC DEVICE

(71) Applicant: KYOCERA Corporation, Kyoto-shi, Kyoto (JP)

(72) Inventor: Shinsuke Moriai, Daito (JP)

(73) Assignee: KYOCERA Corporation, Kyoto (JP)

( * ) Notice: Subject to any disclaimer, the term of this patent is extended or adjusted under 35 U.S.C. 154(b) by 0 days.

(21) Appl. No.: 15/081,714

(22) Filed: Mar. 25, 2016

(65) Prior Publication Data

US 2016/0284192 A1    Sep. 29, 2016

(30) Foreign Application Priority Data

Mar. 27, 2015 (JP) .................................. 2015-066404

(51) Int. Cl.
   *G08B 21/00*   (2006.01)
   *G08B 21/18*   (2006.01)
   *G01N 33/18*   (2006.01)

(52) U.S. Cl.
   CPC ............. *G08B 21/18* (2013.01); *G01N 33/18* (2013.01)

(58) Field of Classification Search
   CPC .......... G08B 21/20; G01N 5/025; H04M 1/18
   USPC ................. 340/604, 605, 618, 815.4; 455/73
   See application file for complete search history.

(56) References Cited

U.S. PATENT DOCUMENTS

| | | | |
|---|---|---|---|
| 2006/0208914 A1* | 9/2006 | Liu | H04M 1/18 340/620 |
| 2008/0134768 A1* | 6/2008 | Sanford | G01N 31/222 73/73 |
| 2013/0182360 A1* | 7/2013 | Stevens | H02H 5/00 361/71 |
| 2013/0225237 A1* | 8/2013 | Minami | H04W 52/0245 455/556.1 |
| 2015/0382305 A1* | 12/2015 | Drincic | H04W 52/0209 455/574 |

FOREIGN PATENT DOCUMENTS

JP     2014-192560 A    10/2014

* cited by examiner

*Primary Examiner* — Phung Nguyen
(74) *Attorney, Agent, or Firm* — Procopio Cory Hargreaves and Savitch LLP

(57) ABSTRACT

A water immersion detection unit detects that an electronic device has been immersed in water. If it is detected that the electronic device has been immersed in water, a salt detection unit measures the salt concentration. A processor makes a determination whether or not the electronic device has been immersed in seawater based on the salt concentration. The processor determines whether or not the electronic device should be washed in water based on a result of the determination whether or not the electronic device has been immersed in seawater. The processor causes a display to display a warning if it is determined that the electronic device should be washed in water.

15 Claims, 22 Drawing Sheets

ELECTRONIC DEVICE

CROSS-REFERENCE TO RELATED APPLICATION

The present application claims priority under 35 U.S.C. §119 to Japanese Patent Application No. 2015-066404, filed on Mar. 27, 2015, entitled "Electronic Device". The content of which is incorporated by reference herein in its entirety.

FIELD

The present disclosure relates to an electronic device.

BACKGROUND

An electronic device having a waterproof structure is known. For example, a certain portable terminal has a housing member having a plurality of openings, a circuit board inserted and fixed to be located in at least a first opening among the plurality of openings, and a sheet-like member bonded so as to close the first opening.

SUMMARY

An electronic device of an embodiment includes a display, a water immersion detection unit configured to detect that the electronic device has been immersed in water, a salt detection unit configured to measure a salt concentration if it is detected that the electronic device has been immersed in water, and a processor configured to make a determination whether or not the electronic device has been immersed in seawater based on the salt concentration, to determine whether or not the electronic device should be washed in water based on a result of the determination, and if it is determined that the electronic device should be washed in water, to cause the display to display a warning.

An electronic device of another embodiment includes a display, a water immersion detection unit configured to detect that the electronic device has been immersed in water, a position detection unit configured to detect a current position of the electronic device if it is detected that the electronic device has been immersed in water, and a processor configured to make a determination whether or not the electronic device has been immersed in seawater based on the current position, to determine whether or not the electronic device should be washed in water based on a result of the determination, and if it is determined that the electronic device should be washed in water, to cause the display to display a warning.

The foregoing and other objects, features, aspects and advantages of the present disclosure will become more apparent from the following detailed description of the present disclosure when taken in conjunction with the accompanying drawings.

DETAILED DESCRIPTION

Hereinafter, the present disclosure will be described with reference to the drawings.

First Embodiment

If a smartphone 1 is immersed in seawater, salt crystals will be left after smartphone 1 is dried. Without being washed in water, performance of smartphone 1 may be adversely affected. For example, if salt crystals remain at a mesh part of a speaker 9 or the like, acoustic performance will be degraded. Smartphone 1 of a first embodiment, if immersed in seawater, can prompt a user to perform water washing, which can solve such a problem.

Figure 1:
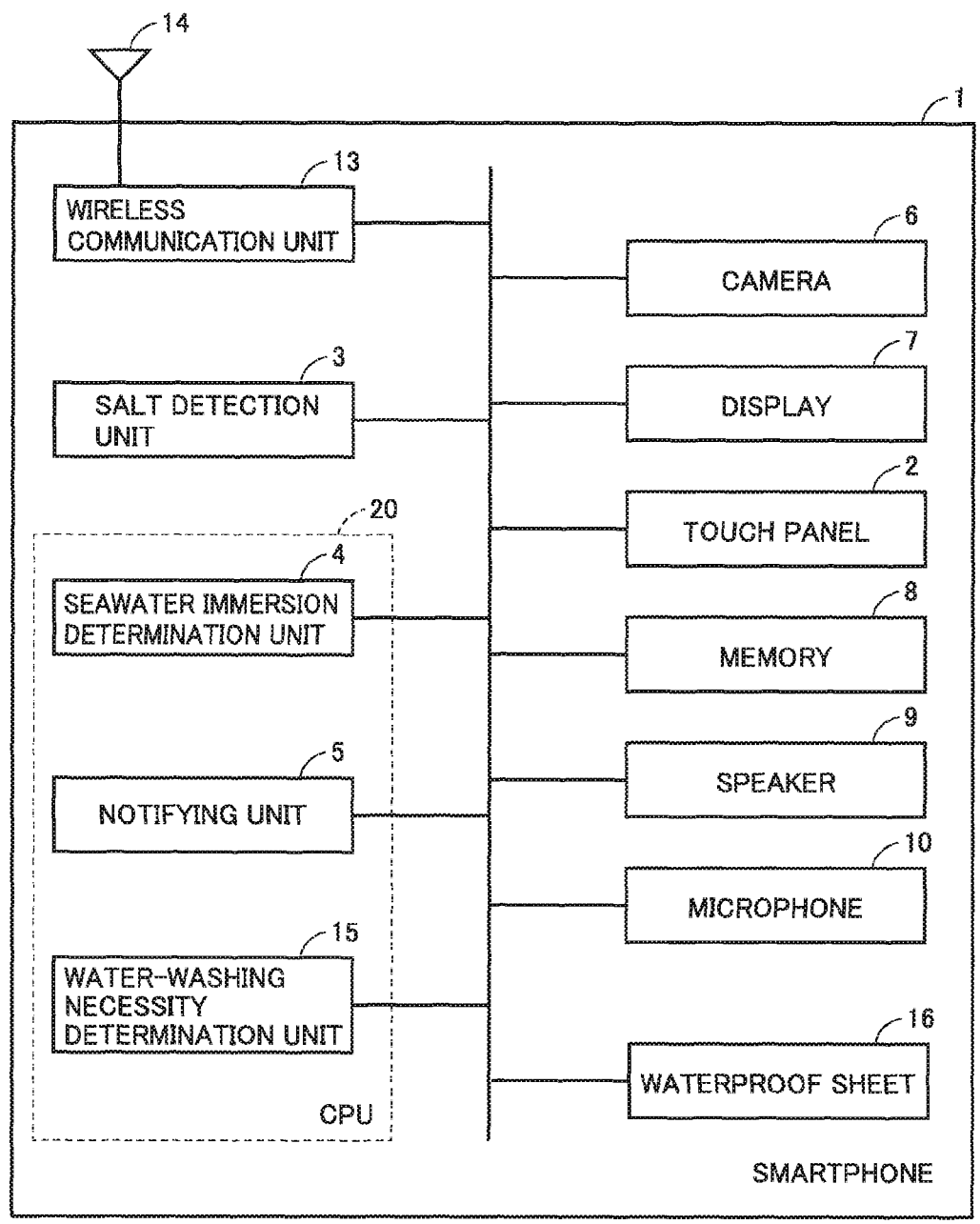
FIG. 1 represents a configuration of a smartphone of a first embodiment.

FIG. 1 represents a configuration of smartphone 1 of the first embodiment.

Referring to FIG. 1, smartphone 1 includes an antenna 14, a wireless communication unit 13, a camera 6, a display 7, a touch panel 2, a memory 8, a speaker 9, a microphone 10, a salt detection unit 3, a seawater immersion determination unit 4, a notifying unit 5, a water-washing necessity determination unit 15, and a waterproof sheet 16.

Seawater immersion determination unit 4, water-washing necessity determination unit 15 and notifying unit 5 can be implemented by a CPU (Central Processing Unit) 20 or the like that executes a program stored in memory 8.

Wireless communication unit 13 can make communications with a base station through antenna 14.

Speaker 9 can output voice of a call partner.

Microphone 10 can receive voice of a user of smartphone 1, and the like.

Camera 6 can pick up an image of a subject.

Display 7 can be implemented by a liquid crystal display, for example.

Touch panel 2 can receive a user input. Touch panel 2 is a capacitance touch panel. Touch panel 2 is provided on a surface of display 7.

Memory 8 can store various types of data.

Waterproof sheet 16 is bonded so as to close an opening of smartphone 1, and can protect the opening from water.

A conventional smartphone having a waterproof function can prevent water from entering the inside thereof, but cannot detect that the smartphone has been immersed in seawater to prompt a user to perform water washing. According to the first embodiment, salt detection unit 3, seawater immersion determination unit 4, water-washing necessity determination unit 15, and notifying unit 5 can solve such a problem.

Salt detection unit 3 can detect the salt concentration of salt water around smartphone 1.

Seawater immersion determination unit 4 determines whether or not smartphone 1 has been immersed in seawater based on the salt concentration detected by salt detection unit 3.

Water-washing necessity determination unit 15 determines whether or not smartphone 1 should be washed in water based on the result of determination made by seawater immersion determination unit 4.

If it is determined that smartphone 1 should be washed in water, notifying unit 5 causes display 7 to display a warning.

Figure 2:
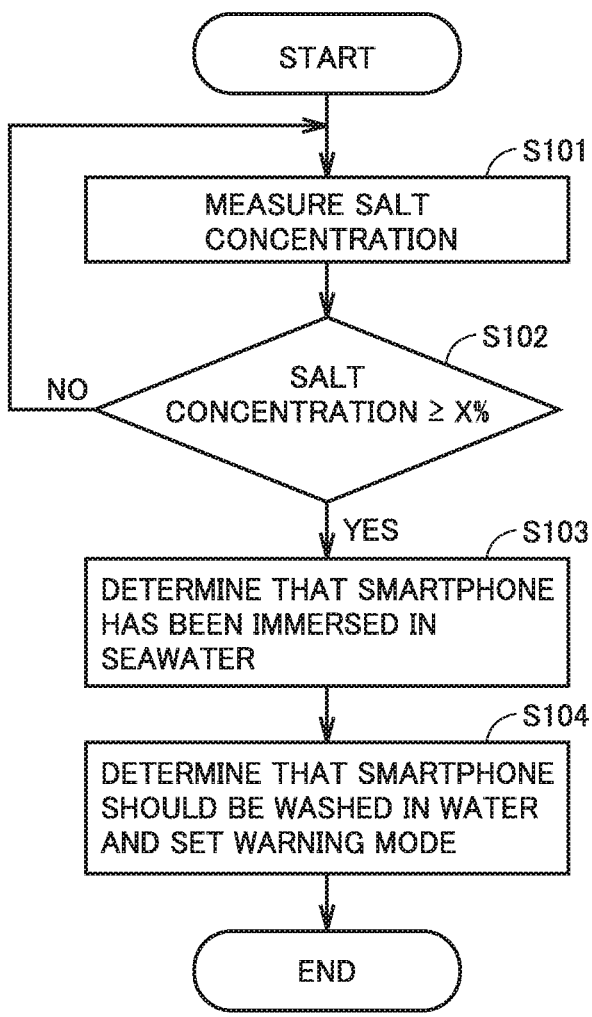
FIG. 2 is a flowchart representing a procedure of determining whether or not the smartphone should be washed in water according to the first embodiment.

FIG. 2 is a flowchart representing a procedure of determining whether or not smartphone 1 should be washed in water according to the first embodiment.

First, in step S101, salt detection unit 3 can detect the salt concentration of salt water around smartphone 1.

In step S102, if the detected salt concentration is more than or equal to a predetermined value X % (YES in S102), seawater immersion determination unit 4 advances the process to step S103, and if the detected salt concentration is less than the predetermined value X % (NO in S102), returns the process to step S101.

In step S103, seawater immersion determination unit 4 can determine that smartphone 1 has been immersed in seawater.

In step S104, water-washing necessity determination unit 15 can determine that smartphone 1 should be washed in water, and can set the current mode into a warning mode.

Figure 3:
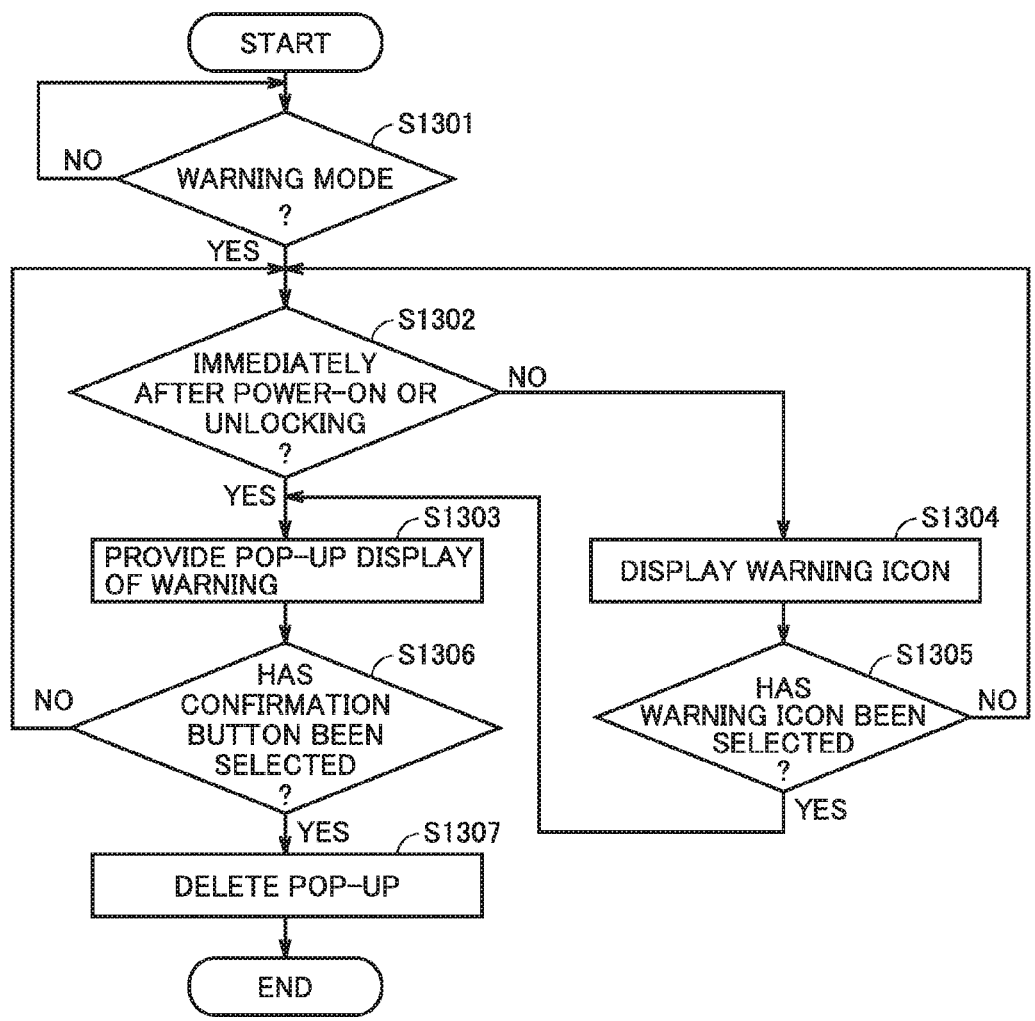
FIG. 3 is a flowchart representing a procedure of warning that the smartphone should be washed in water according to the first embodiment.
Figure 4:
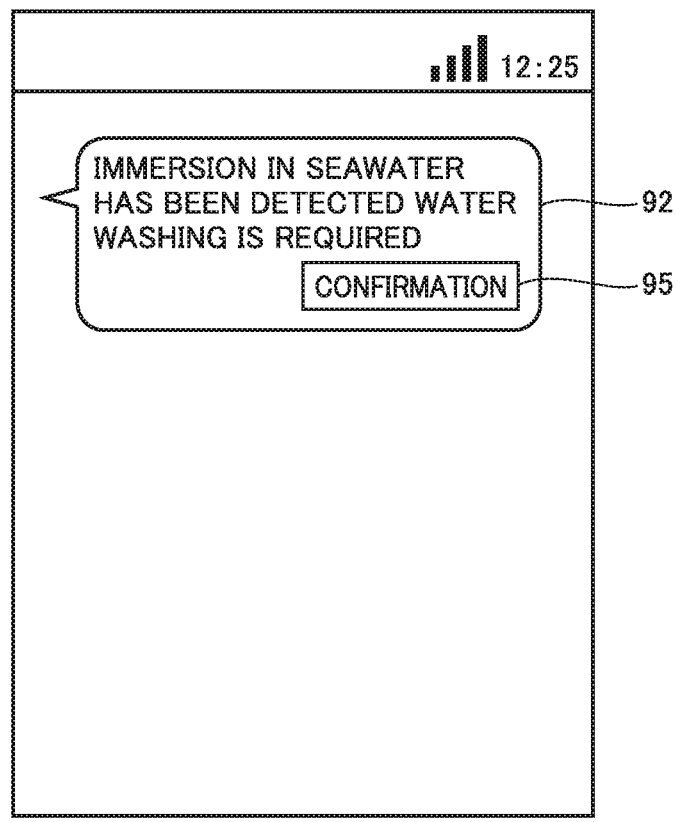
FIG. 4 represents an example of a pop-up display of a warning.
Figure 5:
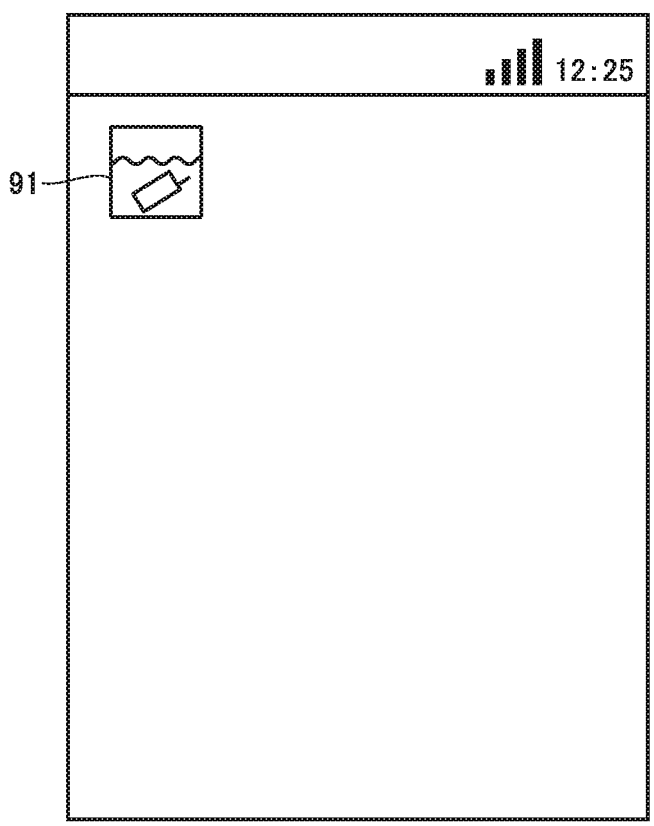
FIG. 5 represents an example of a warning icon.

FIG. 3 is a flowchart representing a procedure of warning that smartphone 1 should be washed in water according to the first embodiment. FIG. 4 represents an example of a pop-up display of a warning. FIG. 5 represents an example of a warning icon.

Referring to FIGS. 3 to 5, if the warning mode has been set in step S1301 (YES in S1301), the process proceeds into step S1302.

In step S1302, if it is immediately after smartphone 1 is powered on or immediately after smartphone 1 is unlocked (YES in S1302), the process proceeds into step S1303, and otherwise (NO in S1302), the process proceeds into step S1304.

In step S1303, notifying unit 5 can cause display 7 to provide a pop-up display of a warning as shown in FIG. 4. In the example of FIG. 4, a warning 92 and a confirmation button 95 are displayed.

In step S1304, notifying unit 5 can cause display 7 to display a warning icon as shown in FIG. 5. In the example of FIG. 5, a warning icon 91 is displayed.

Following step S1304, in step S1305, if the warning icon has been selected by a user operation on touch panel 2 (YES in S1305), the process proceeds into above-described step S1303.

Following step S1303, in step S1306, if the confirmation button included in the pop-up has been selected by a user operation on touch panel 2 (YES in S1306), the process proceeds into step S1307.

In step S1307, notifying unit 5 can delete the pop-up display of the warning.

As described above, the first embodiment detects the salt concentration of salt water around smartphone 1, determines whether or not smartphone 1 has been immersed in seawater based on the detected salt concentration, and if it is determined that smartphone 1 has been immersed in seawater, displays a warning. If a user washes smartphone 1 in water in accordance with the warning, degradation of performance of smartphone 1 such as acoustic performance can be prevented.

Variation of First Embodiment

Figure 6:
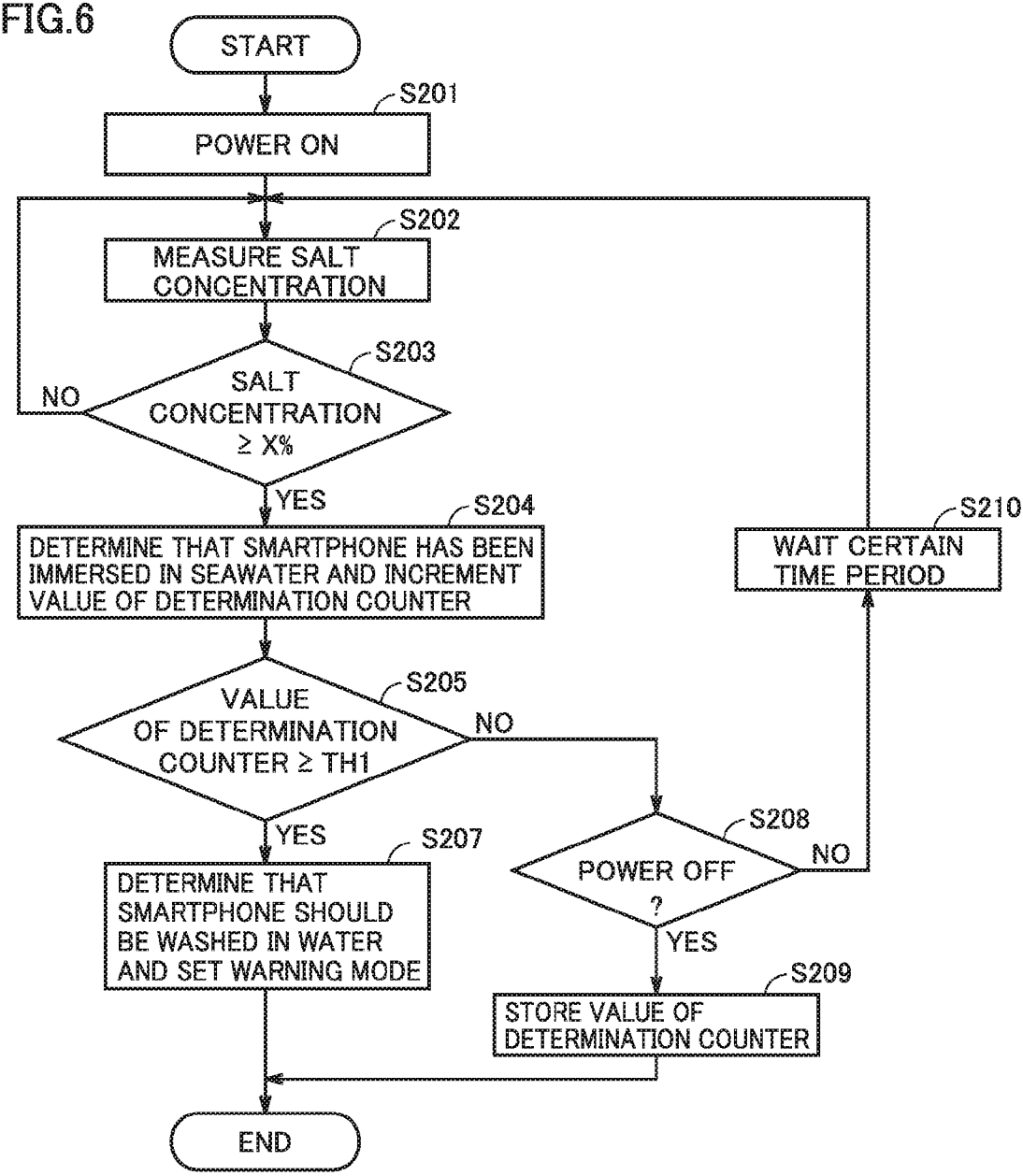
FIG. 6 is a flowchart representing a procedure of determining whether or not a smartphone should be washed in water according to a variation of the first embodiment.

FIG. 6 is a flowchart representing a procedure of determining whether or not a smartphone should be washed in water according to a variation of the first embodiment.

In step S201, smartphone 1 is powered on.

In step S202, salt detection unit 3 can detect the salt concentration around smartphone 1.

In step S203, if the detected salt concentration is more than or equal to the predetermined value X % (YES in S203), seawater immersion determination unit 4 advances the process to step S204, and if the detected salt concentration is less than the predetermined value X % (NO in S203), returns the process to step S202.

In step S204, seawater immersion determination unit 4 can determine that smartphone 1 has been immersed in seawater, and can increment the value of a determination counter.

In step S205, if the value of the determination counter is more than or equal to a threshold value TH1 (YES in S205), the process proceeds into step S206, and if the value of the determination counter is less than threshold value TH1 (NO in S205), the process proceeds into step S208.

In step S207, water-washing necessity determination unit 15 can determine that smartphone 1 should be washed in water, and can set the current mode into the warning mode.

In step S208, if smartphone 1 is powered off (YES in S208), the process proceeds into step S209, and if smartphone 1 is left powered on (NO in S208), the process proceeds into step S210.

In step S209, seawater immersion determination unit 4 causes memory 8 to store the value of the determination counter. Accordingly, reading the stored value of the determination counter next time when smartphone 1 is powered on allows counting to be achieved with the number of times that the smartphone has been immersed in seawater reflected.

After the process waits a certain time period in step S210, the process is returned to step S202.

As described above, this variation notifies a warning to wash smartphone 1 in water if it is determined that the number of times of immersion in seawater is more than or equal to a threshold value based on the detected result of the salt concentration. Thus, it is particularly effective in such a case where accumulated salt crystals increase as the number of times that smartphone 1 has been immersed in seawater is larger.

Second Embodiment

Figure 7:
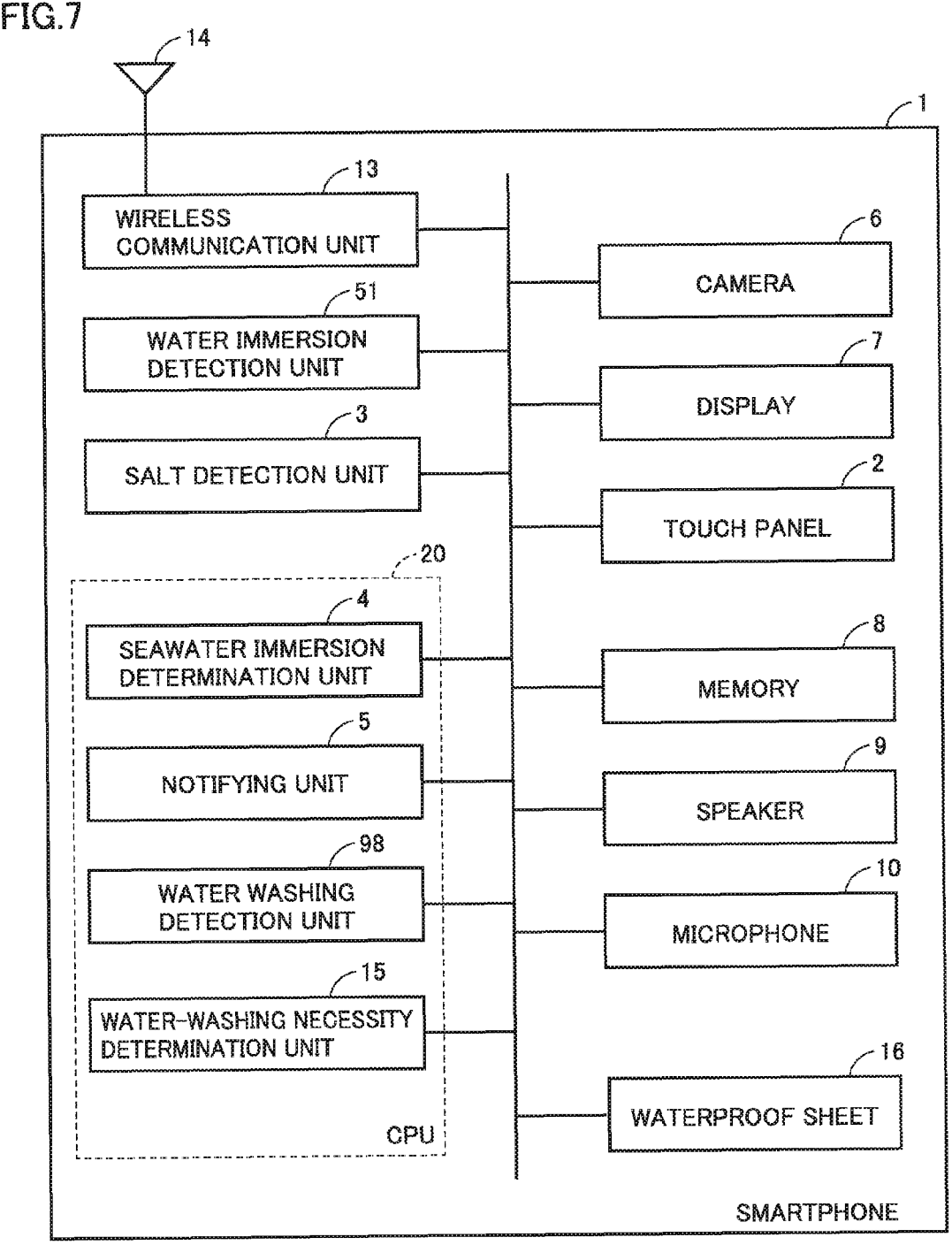
FIG. 7 represents a configuration of a smartphone of a second embodiment.

FIG. 7 represents a configuration of smartphone 1 of a second embodiment.

As shown in FIG. 7, smartphone 1 of the second embodiment further includes a water immersion detection unit 51 and a water washing detection unit 98, in addition to the configuration of smartphone 1 of the first embodiment shown in FIG. 1.

In the second embodiment, touch panel 2 is used not only to receive a user input but also to detect that smartphone 1 has been immersed in water.

Water immersion detection unit 51 can detect whether or not smartphone 1 has been immersed in water based on the capacitance of touch panel 2. Specifically, water immersion detection unit 51 detects that smartphone 1 has been immersed in water when the capacitance becomes more than or equal to a predetermined value TH2 and less than threshold value TH1 in the entire region of touch panel 2. Threshold value TH1 is a threshold value for detecting that a user has touched touch panel 2 with his/her finger.

After it is determined that smartphone 1 has been immersed in seawater and if water immersion detection unit 51 has detected water immersion and the salt concentration detected by salt detection unit 3 is less than or equal to Y %, water washing detection unit 98 detects that smartphone 1 has been washed in water.

Figure 8:
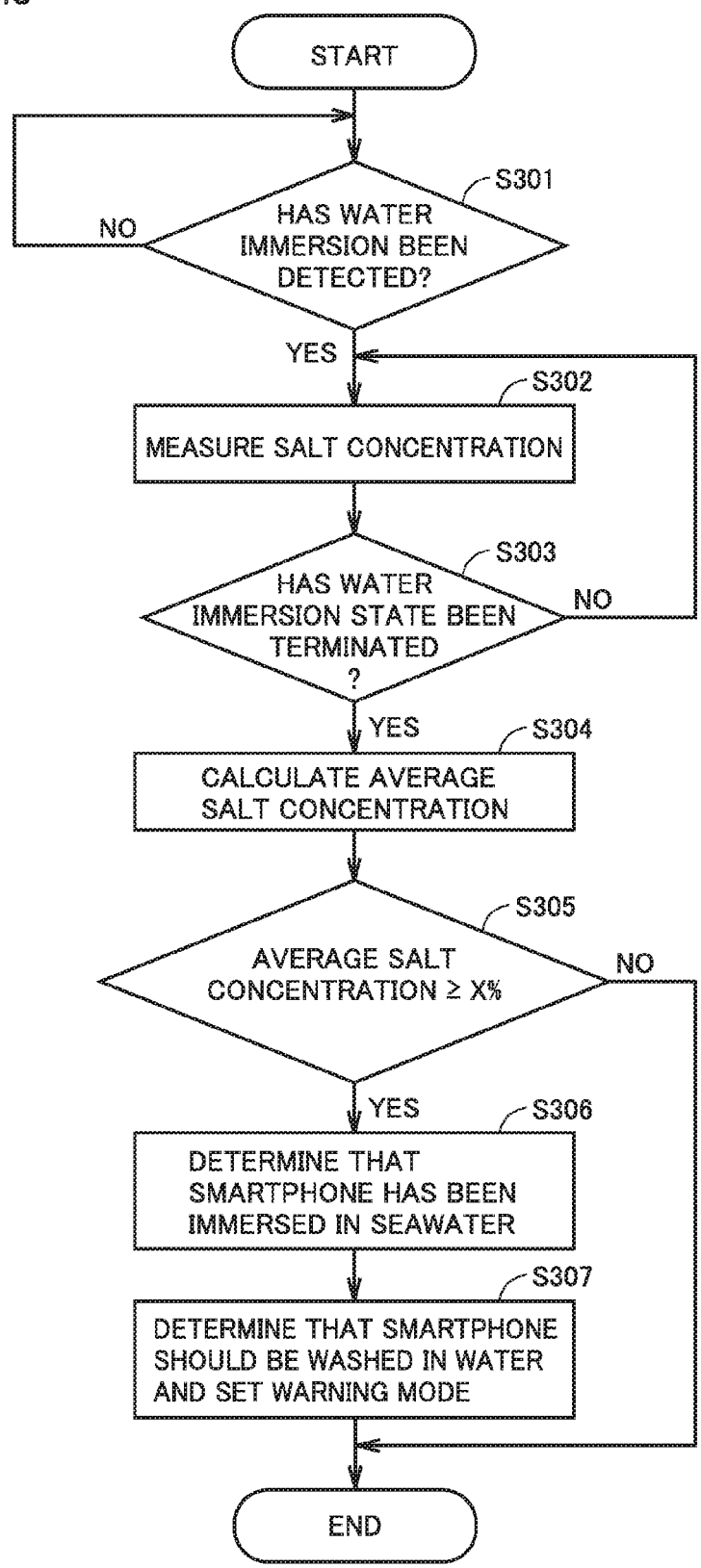
FIG. 8 is a flowchart representing a procedure of determining whether or not the smartphone should be washed in water according to the second embodiment.

FIG. 8 is a flowchart representing a procedure of determining whether or not smartphone 1 should be washed in water according to the second embodiment.

In step S301, if water immersion detection unit 51 detects that smartphone 1 has been immersed in water (YES in S301), the process proceeds into step S302.

In step S302, salt detection unit 3 can detect the salt concentration around smartphone 1.

In step S303, if water immersion detection unit 51 detects that water immersion of smartphone 1 has been terminated (YES in S303), the process proceeds into step S304.

In step S304, seawater immersion determination unit 4 can calculate an average salt concentration during water immersion of smartphone 1.

In step S305, if the average salt concentration is more than or equal to the predetermined value X % (YES in S305), seawater immersion determination unit 4 advances the process to step S306.

In step S306, seawater immersion determination unit 4 can determine that smartphone 1 has been immersed in seawater.

In step S307, water-washing necessity determination unit 15 can determine that smartphone 1 should be washed in water, and can set the current mode into the warning mode.

Figure 9:
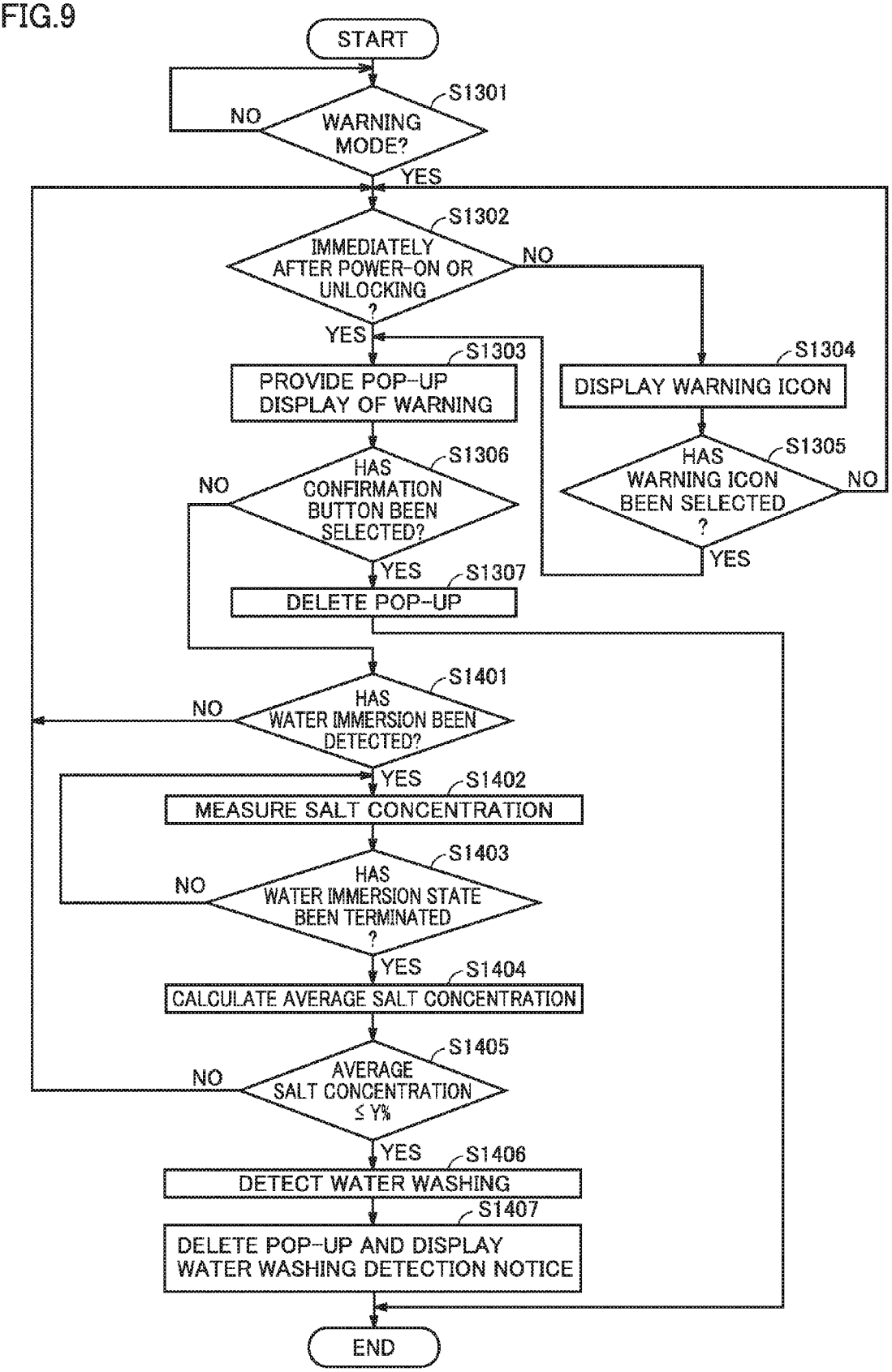
FIG. 9 is a flowchart representing a procedure of warning that the smartphone should be washed in water according to the second embodiment.
Figure 10:
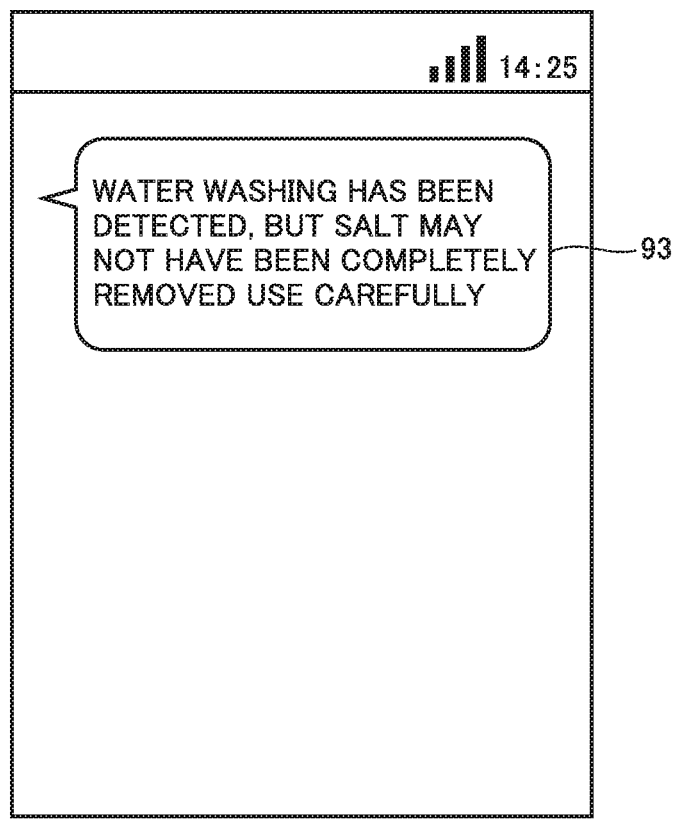
FIG. 10 represents an example of a water washing detection notice.

FIG. 9 is a flowchart representing a procedure of warning that smartphone 1 should be washed in water according to the second embodiment. FIG. 10 represents an example of a water washing detection notice.

The flowchart of FIG. 9 differs from that of FIG. 3 according to the first embodiment in that steps S1401 to S1407 have been added.

Referring to FIGS. 9 and 10, if NO in step S1306, and if water immersion detection unit 51 detects that smartphone 1 has been immersed in water in step S1401 (YES in S1401), the process proceeds into step S1402.

In step S1402, salt detection unit 3 can detect the salt concentration around smartphone 1.

In step S1403, if water immersion detection unit 51 detects that water immersion of smartphone 1 has been terminated (YES in S1403), the process proceeds into step S1404.

In step S1404, seawater immersion determination unit 4 calculates an average salt concentration during water immersion of smartphone 1.

In step S1405, if the average salt concentration is less than or equal to the predetermined value Y % (YES in S1405), seawater immersion determination unit 4

In step S1406, water washing detection unit 98 can detect that smartphone 1 has been washed in water.

In step S1407, notifying unit 5 can delete the pop-up display of the warning. Notifying unit 5 can cause display 7 to display a water washing detection notice as shown in FIG. 10. In the example of FIG. 10, a message 93 is displayed which reads that water washing has been detected but recommends continuing to use smartphone 1 carefully.

As described above, the second embodiment measures the salt concentration with detection of water immersion serving as a trigger, which can avoid a situation in which salt detection unit 3 always has to measure the salt concentration. The second embodiment can automatically delete the warning if it is detected that smartphone 1 has been washed in water, which can avoid user effort to manually delete the warning.

Variation of Second Embodiment

Figure 11:
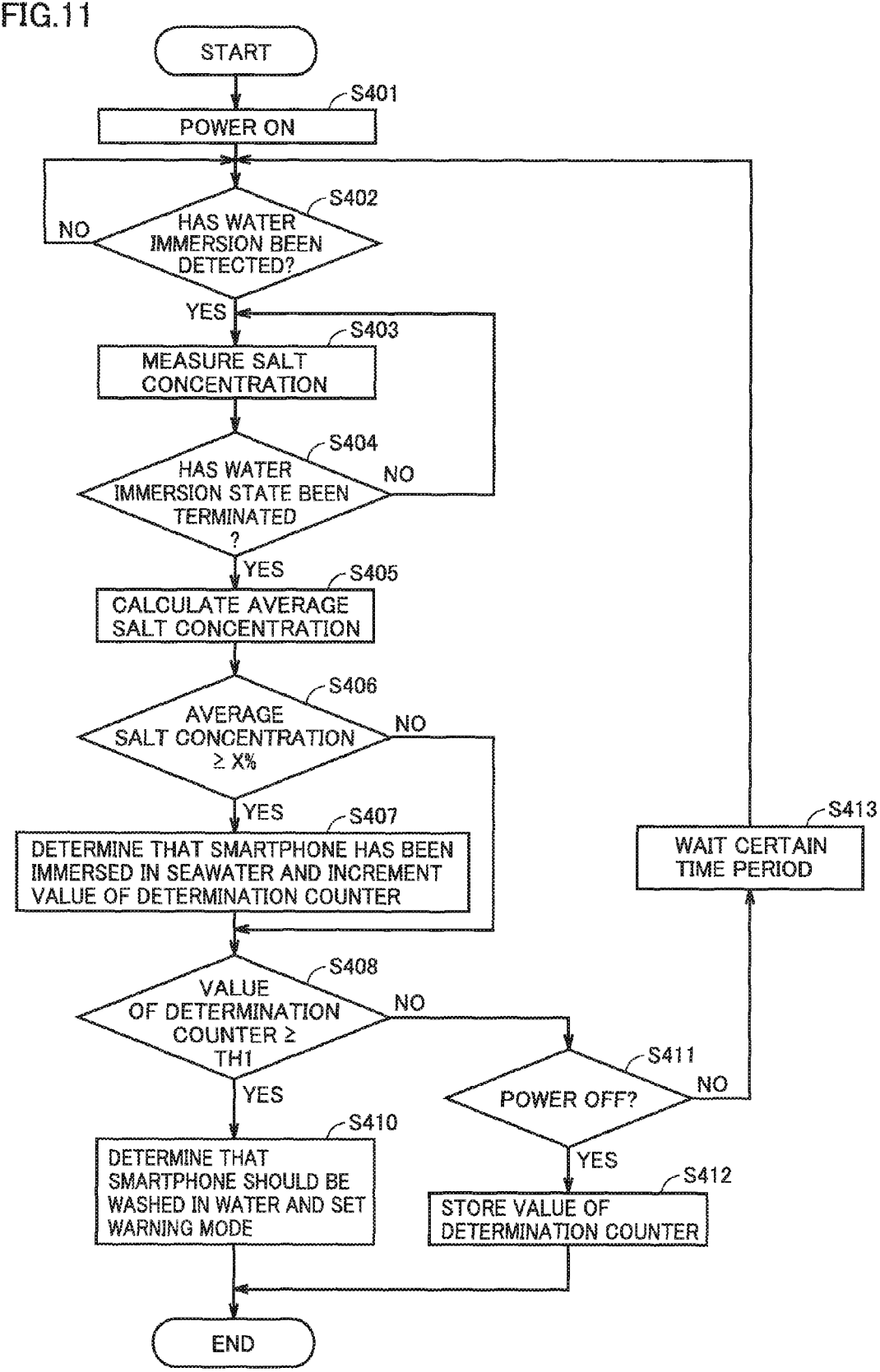
FIG. 11 is a flowchart representing a procedure of determining whether or not a smartphone should be washed in water according to a variation of the second embodiment.

FIG. 11 is a flowchart representing a procedure of determining whether or not smartphone 1 should be washed in water according to a variation of the second embodiment.

In step S401, smartphone 1 is powered on.

In step S402, if water immersion detection unit 51 detects that smartphone 1 has been immersed in water (YES in S402), the process proceeds into step S403.

In step S403, salt detection unit 3 can detect the salt concentration around smartphone 1.

In step S404, if water immersion detection unit 51 detects that water immersion of smartphone 1 has been terminated (YES in S404), the process proceeds into step S405.

In step S405, seawater immersion determination unit 4 calculates an average salt concentration during water immersion of smartphone 1.

In step S406, if the average salt concentration is more than or equal to the predetermined value X %, seawater immersion determination unit 4 advances the process to step S407.

In step S407, seawater immersion determination unit 4 can determine that smartphone 1 has been immersed in seawater, and can increment the value of the determination counter.

In step S408, if the value of the determination counter is more than or equal to threshold value TH1 (YES in S408), the process proceeds into step S409, and if the value of the determination counter is less than threshold value TH1 (NO in S408), the process proceeds into step S411.

In step S410, water-washing necessity determination unit 15 can determine that smartphone 1 should be washed in water, and can set the current mode into the warning mode.

In step S411, if smartphone 1 is powered off (YES in S411), the process proceeds into step S412, and if smartphone 1 is left powered on (NO in S411), the process proceeds into step S413.

In step S412, seawater immersion determination unit 4 causes memory 8 to store the value of the determination counter.

After the process waits a certain time period in step S413, the process is returned to step S402.

As described above, this variation notifies a warning to wash smartphone 1 in water if it is determined that the number of times that smartphone 1 has been immersed in seawater is more than or equal to a threshold value based on whether or not smartphone 1 has been immersed in water and the detected result of the salt concentration. Thus, it is particularly effective in such a case where accumulated salt crystals increase as the number of times that smartphone 1 has been immersed in seawater is larger.

Third Embodiment

Figure 12:
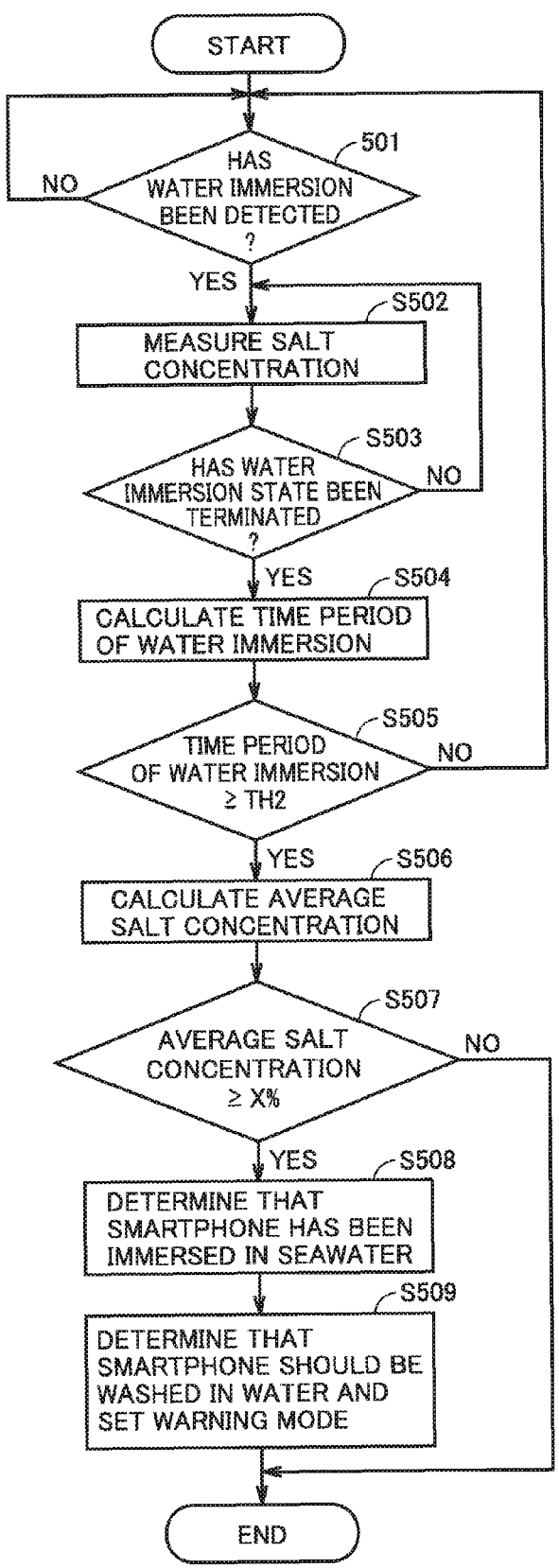
FIG. 12 is a flowchart representing a procedure of determining whether or not a smartphone should be washed in water according to a third embodiment.

FIG. 12 is a flowchart representing a procedure of determining whether or not smartphone 1 should be washed in water according to a third embodiment.

In step S501, if water immersion detection unit 51 detects that smartphone 1 has been immersed in water (YES in S501), the process proceeds into step S502.

In step S502, salt detection unit 3 can detect the salt concentration around smartphone 1.

In step S503, if water immersion detection unit 51 detects that water immersion of smartphone 1 has been terminated (YES in S503), the process proceeds into step S504.

In step S504, seawater immersion determination unit 4 can calculate the time period in which smartphone 1 has been immersed in water.

In step S505, if the time period in which smartphone 1 has been immersed in water is more than or equal to predetermined value TH2 (YES in S505), the process proceeds into step S506.

In step S506, seawater immersion determination unit 4 can calculate an average salt concentration during water immersion of smartphone 1.

In step S507, if the average salt concentration is more than or equal to the predetermined value X % (YES in S507), seawater immersion determination unit 4 advances the process to step S508.

In step S508, seawater immersion determination unit 4 can determine that smartphone 1 has been immersed in seawater.

In step S509, water-washing necessity determination unit 15 can determine that smartphone 1 should be washed in water, and can set the current mode into the warning mode.

Figure 13:
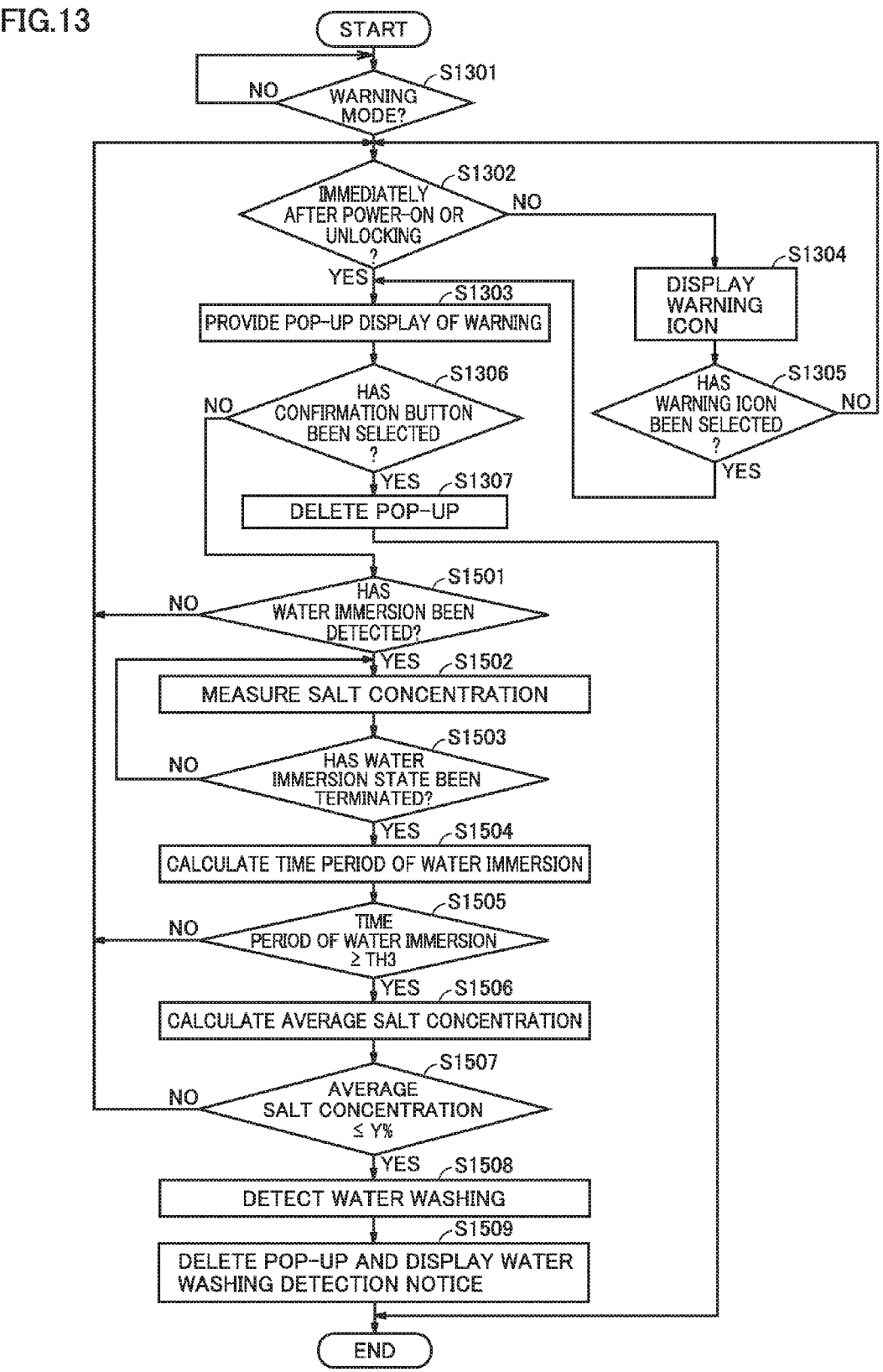
FIG. 13 is a flowchart representing a procedure of warning that the smartphone should be washed in water according to the third embodiment.

FIG. 13 is a flowchart representing a procedure of warning that smartphone 1 should be washed in water according to the third embodiment.

The flowchart of FIG. 13 differs from that of FIG. 3 according to the first embodiment in that steps S1501 to S1509 have been added.

Referring to FIG. 13, if NO in step S1306, and if water immersion detection unit 51 detects that smartphone 1 has been immersed in water in step S1501 (YES in S1501), the process proceeds into step S1502.

In step S1502, salt detection unit 3 can detect the salt concentration around smartphone 1.

In step S1503, if water immersion detection unit 51 detects that water immersion of smartphone 1 has been terminated (YES in S1503), the process proceeds into step S1504.

In step S1504, seawater immersion determination unit 4 can calculate the time period in which smartphone 1 has been immersed in water.

In step S1505, if the time period in which smartphone 1 has been immersed in water is more than or equal to a predetermined value TH3 (YES in S1505), the process proceeds into step S1506.

In step S1506, seawater immersion determination unit 4 calculates an average salt concentration during water immersion of smartphone 1.

In step S1507, if the average salt concentration is less than or equal to the predetermined value Y % (YES in S1507), seawater immersion determination unit 4 advances the process to step S1508.

In step S1508, water washing detection unit 98 can detect that smartphone 1 has been washed in water.

In step S1509, notifying unit 5 can delete the pop-up display of the warning. Notifying unit 5 can cause display 7 to display a water washing detection notice as shown in FIG. 10. In the example of FIG. 10, a message is displayed which reads that water washing has been detected but recommends continuing to use smartphone 1 carefully.

As described above, the third embodiment does not determine that smartphone 1 has been immersed in seawater if the time period in which smartphone 1 has been immersed in water is more than or equal to the threshold value. Thus, it is particularly effective in such a case where salt crystals are less likely to be left after drying smartphone 1 having been immersed in seawater for only a short while. The third embodiment does not automatically delete the warning if it is not detected that smartphone 1 has been washed in water for a predetermined time period or longer. Thus, it is particularly effective in such a case where salt crystals cannot be removed only by washing in water for a short while.

Variation of Third Embodiment

Figure 14:
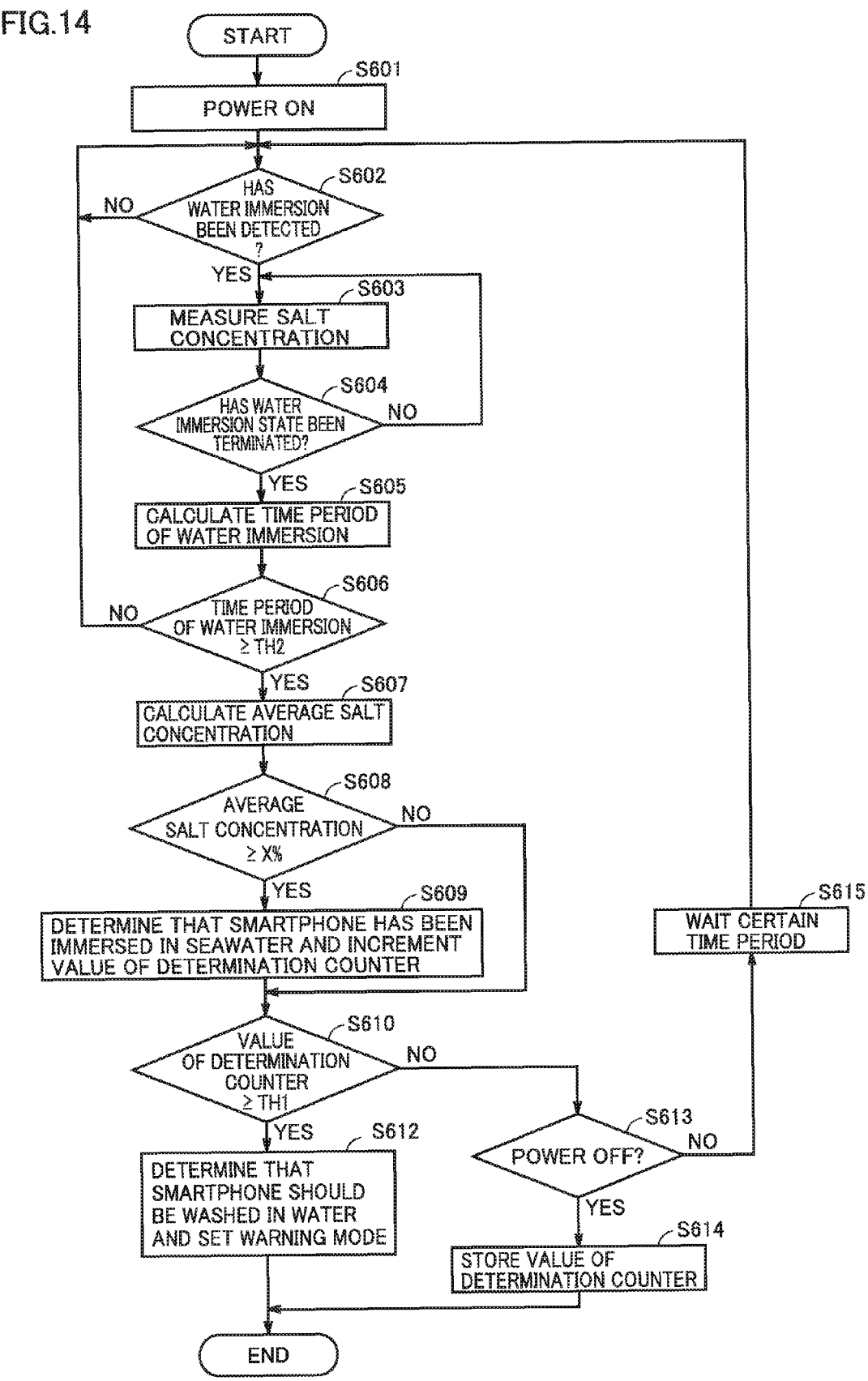
FIG. 14 is a flowchart representing a procedure of determining whether or not a smartphone should be washed in water according to a variation of the third embodiment.

FIG. 14 is a flowchart representing a procedure of determining whether or not smartphone 1 should be washed in water according to a variation of the third embodiment.

In step S601, smartphone 1 is powered on.

In step S602, if water immersion detection unit 51 detects that smartphone 1 has been immersed in water (YES in S602), the process proceeds into step S603.

In step S603, salt detection unit 3 can detect the salt concentration around smartphone 1.

In step S604, if water immersion detection unit 51 detects that water immersion of smartphone 1 has been terminated (YES in S604), the process proceeds into step S605.

In step S605, seawater immersion determination unit 4 can calculate the time period in which smartphone 1 has been immersed in water.

In step S606, if the time period in which smartphone 1 has been immersed in water is more than or equal to predetermined value TH2 (YES in S606), the process proceeds into step S607.

In step S607, seawater immersion determination unit 4 can calculate an average salt concentration during water immersion of smartphone 1.

In step S608, if the average salt concentration is more than or equal to the predetermined value X % (YES in S608), seawater immersion determination unit 4 advances the process to step S609.

In step S609, seawater immersion determination unit 4 can determine that smartphone 1 has been immersed in seawater, and can increment the value of the determination counter.

In step S610, if the value of the determination counter is more than or equal to threshold value TH1 (YES in S610), the process proceeds into step S611, and if the value of the determination counter is less than threshold value TH1 (NO in S610), the process proceeds into step S613.

In step S612, water-washing necessity determination unit 15 can determine that smartphone 1 should be washed in water, and can set the current mode into the warning mode.

In step S613, if smartphone 1 is powered off (YES in S613), the process proceeds into step S614, and if smartphone 1 is left powered on (NO in S613), the process proceeds into step S615.

In step S614, seawater immersion determination unit 4 causes memory 8 to store the value of the determination counter.

After the process waits a certain time period in step S615, the process is returned to step S602.

As described above, this variation notifies a warning to wash smartphone 1 in water if it is determined that the number of times of immersion in seawater is more than or equal to a threshold value based on the detected results of the time period of water immersion and the salt concentration. Thus, it is particularly effective in such a case where accumulated salt crystals increase as the number of times that smartphone 1 has been immersed in seawater is larger.

Fourth Embodiment

Figure 15:
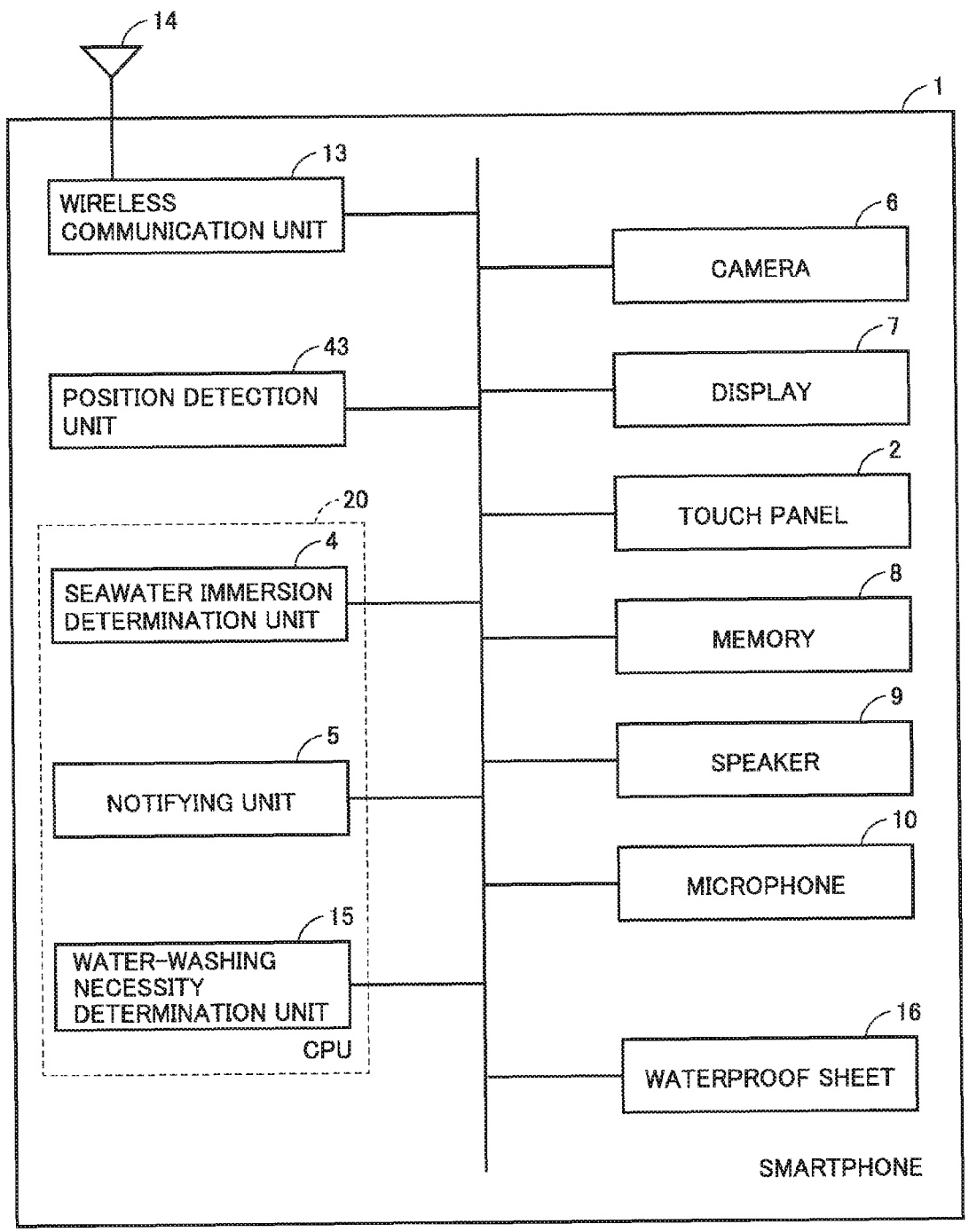
FIG. 15 represents a configuration of a smartphone of a fourth embodiment.

FIG. 15 represents a configuration of smartphone 1 of a fourth embodiment.

As shown in FIG. 15, smartphone 1 of the fourth embodiment includes a position detection unit 43 instead of salt detection unit 3 of smartphone 1 of the first embodiment shown in FIG. 1.

Position detection unit 43 includes a GPS (Global Positioning System) receiver. Position detection unit 43 can detect the current position of smartphone 1 based on data received by the GPS receiver.

Figure 16:
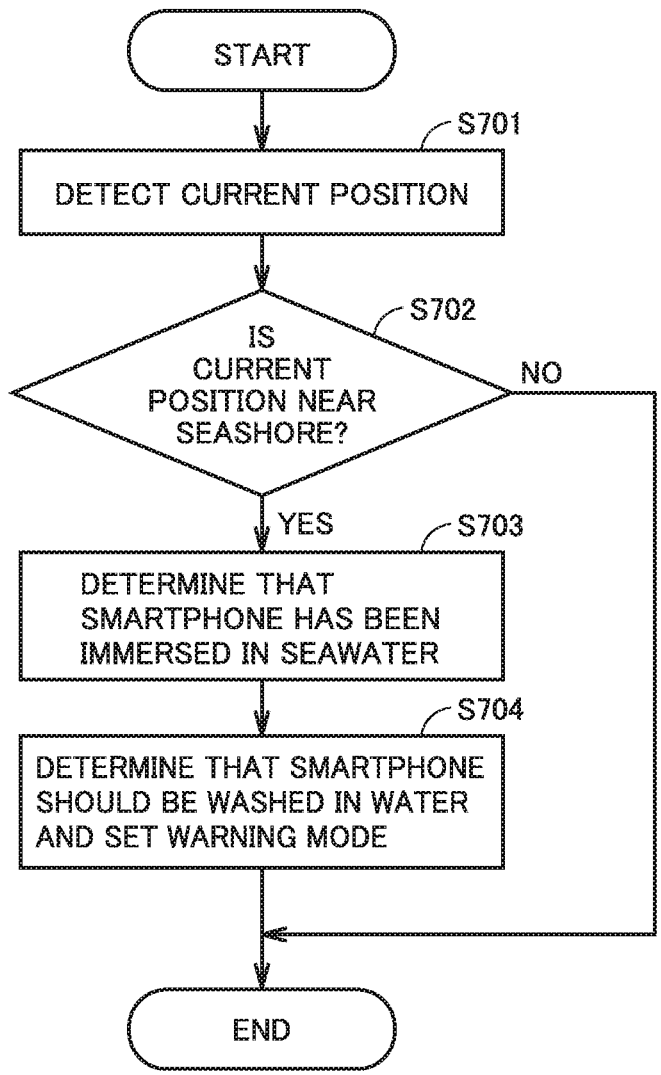
FIG. 16 is a flowchart representing a procedure of determining whether or not the smartphone should be washed in water according to the fourth embodiment.

FIG. 16 is a flowchart representing a procedure of determining whether or not smartphone 1 should be washed in water according to the fourth embodiment.

First, in step S701, position detection unit 43 can detect the current position of smartphone 1.

In step S702, if the current position is near the seashore (YES in S702), seawater immersion determination unit 4 advances the process to step S703.

In step S703, seawater immersion determination unit 4 can determine that smartphone 1 has been immersed in seawater.

In step S704, water-washing necessity determination unit 15 can determine that smartphone 1 should be washed in water, and can set the current mode into the warning mode.

As described above, the fourth embodiment detects the current position of smartphone 1, determines whether or not smartphone 1 has been immersed in seawater based on the current position, and if it is determined that smartphone 1 has been immersed in seawater, displays a warning. If a user washes smartphone 1 in water in accordance with the warning, degradation of performance of smartphone 1 such as acoustic performance can be prevented.

Variation of Fourth Embodiment

Figure 17:
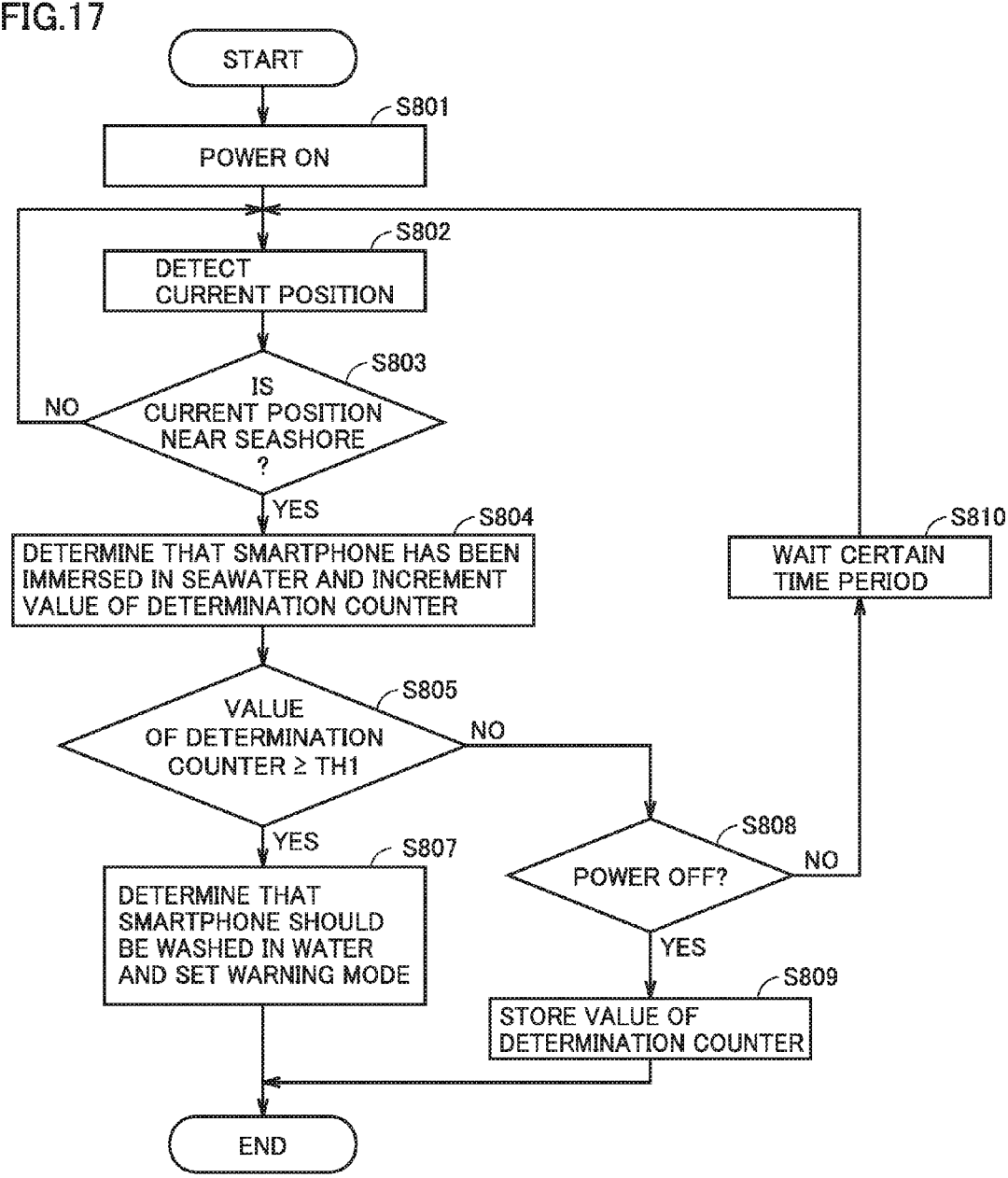
FIG. 17 is a flowchart representing a procedure of determining whether or not a smartphone should be washed in water according to a variation of the fourth embodiment.

FIG. 17 is a flowchart representing a procedure of determining whether or not smartphone 1 should be washed in water according to a variation of the fourth embodiment.

In step S801, smartphone 1 is powered on.

In step S802, position detection unit 43 can detect the current position of smartphone 1.

In step S803, if the current position is near the seashore (YES in S803), seawater immersion determination unit 4 advances the process to step S804.

In step S804, seawater immersion determination unit 4 can determine that smartphone 1 has been immersed in seawater, and can increment the value of the determination counter.

In step S805, if the value of the determination counter is more than or equal to threshold value TH1 (YES in S805), the process proceeds into step S806, and if the value of the determination counter is less than threshold value TH1 (NO in S805), the process proceeds into step S808.

In step S807, water-washing necessity determination unit 15 can determine that smartphone 1 should be washed in water, and can set the current mode into the warning mode.

In step S808, if smartphone 1 is powered off (YES in S808), the process proceeds into step S809, and if smartphone 1 is left powered on (NO in S808), the process proceeds into step S810.

In step S809, seawater immersion determination unit 4 causes memory 8 to store the value of the determination counter.

After the process waits a certain time period in step S810, the process is returned to step S802.

As described above, this variation notifies a warning to wash smartphone 1 in water if it is determined that the number of times of immersion in seawater is more than or equal to a threshold value based on the current position of smartphone 1. Thus, it is particularly effective in such a case where accumulated salt crystals increase as the number of times that smartphone 1 has been immersed in seawater is larger.

Fifth Embodiment

Figure 18:
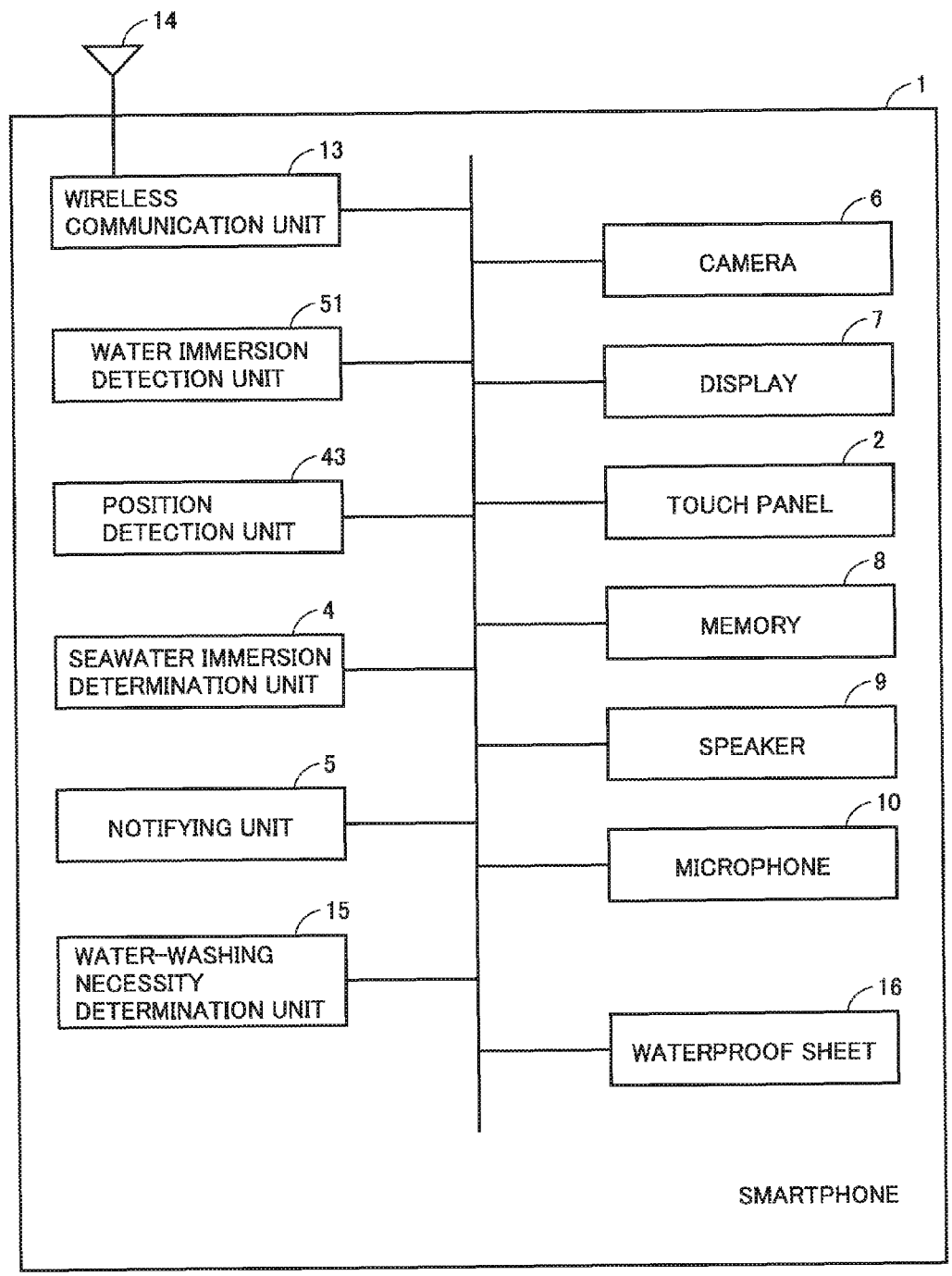
FIG. 18 represents a configuration of a smartphone of a fifth embodiment.

FIG. 18 represents a configuration of smartphone 1 of a fifth embodiment.

As shown in FIG. 18, smartphone 1 of the fifth embodiment further includes a water immersion detection unit 51 in addition to the configuration of smartphone 1 of the fourth embodiment shown in FIG. 15.

Water immersion detection unit 51 can detect whether or not smartphone 1 has been immersed in water based on the capacitance of touch panel 2. Specifically, water immersion detection unit 51 detects that smartphone 1 has been immersed in water when the capacitance becomes more than or equal to predetermined value TH2 and less than threshold value TH1 in the entire region of touch panel 2. Threshold value TH1 is a threshold value for detecting that a user has touched touch panel 2 with his/her finger.

Figure 19:
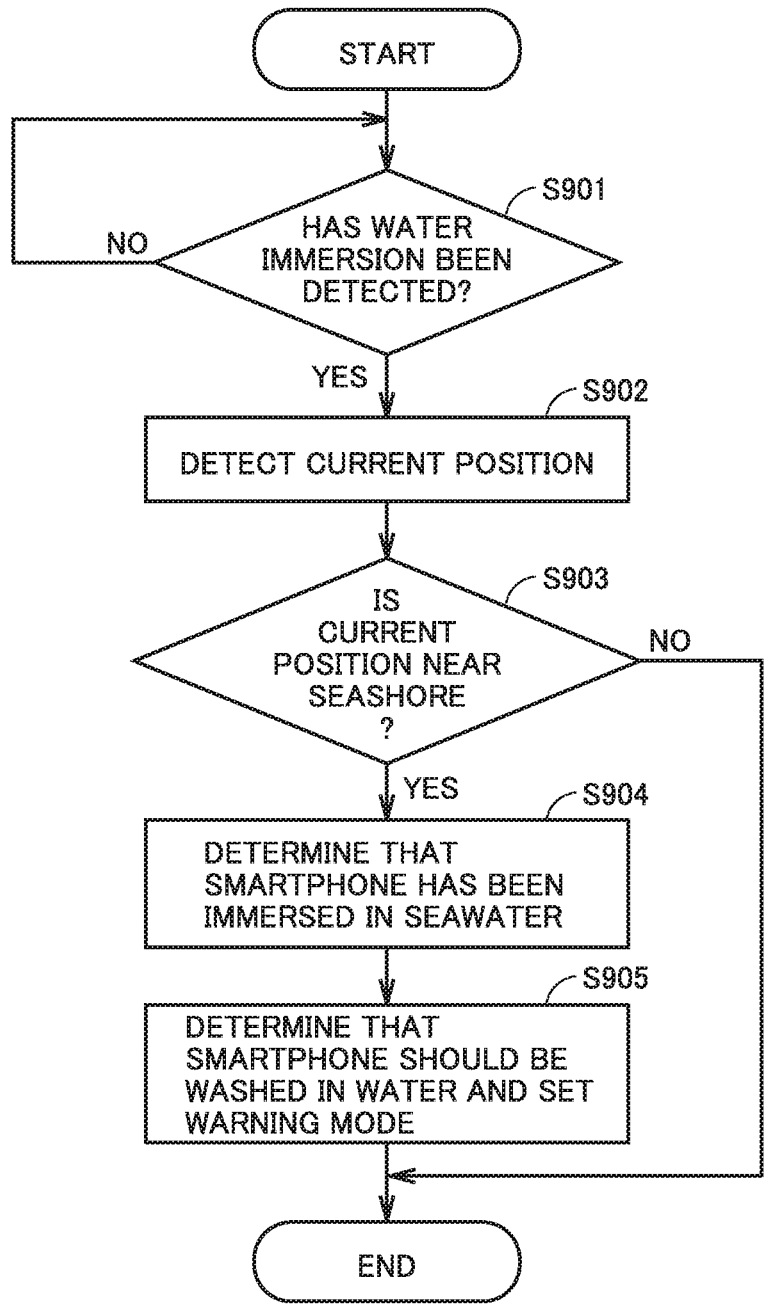
FIG. 19 is a flowchart representing a procedure of determining whether or not the smartphone should be washed in water according to the fifth embodiment.

FIG. 19 is a flowchart representing a procedure of determining whether or not smartphone 1 should be washed in water according to the fifth embodiment.

In step S901, if water immersion detection unit 51 detects that smartphone 1 has been immersed in water (YES in S901), the process proceeds into step S902.

In step S902, position detection unit 43 can detect the current position of smartphone 1.

In step S403, if the current position is near the seashore (YES in S903), seawater immersion determination unit 4 advances the process to step S904.

In step S404, seawater immersion determination unit 4 can determine that smartphone 1 has been immersed in seawater.

In step S905, water-washing necessity determination unit 15 can determine that smartphone 1 should be washed in water, and can set the current mode into the warning mode.

As described above, the fifth embodiment determines that smartphone 1 has been immersed in seawater if water immersion has been detected and if the current position is near the seashore. Thus, it is possible to avoid a determination that smartphone 1 has been immersed in seawater when the current position of smartphone 1 is near the seashore but smartphone 1 actually has not been immersed in seawater.

Variation of Fifth Embodiment

Figure 20:
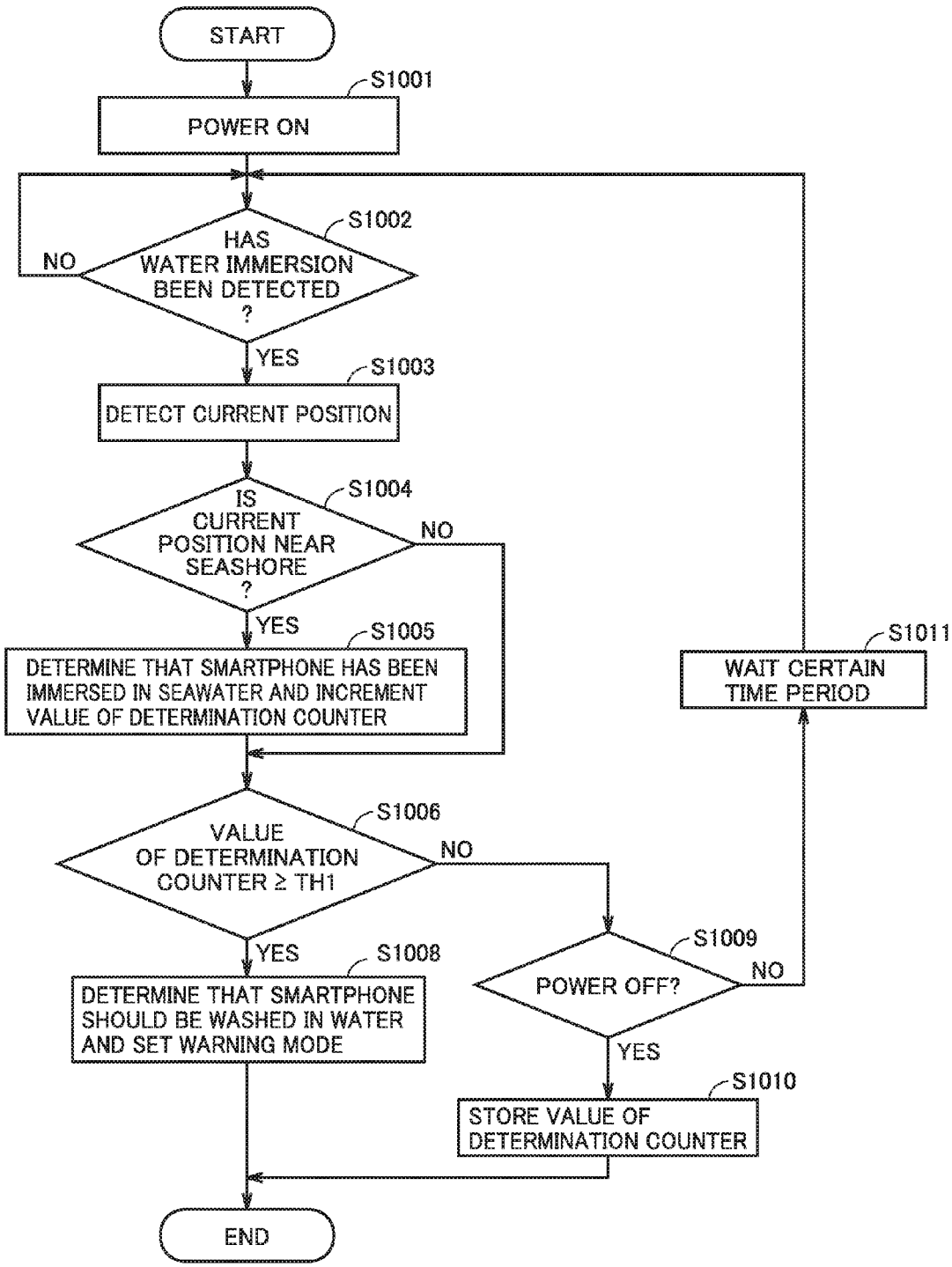
FIG. 20 is a flowchart representing a procedure of determining whether or not smartphone should be washed in water according to a variation of the fifth embodiment.

FIG. 20 is a flowchart representing a procedure of determining whether or not smartphone 1 should be washed in water according to a variation of the fifth embodiment.

In step S1001, smartphone 1 is powered on.

In step S1002, if water immersion detection unit 51 detects that smartphone 1 has been immersed in water (YES in S1001), the process proceeds into step S1002.

In step S1003, position detection unit 43 can detect the current position of smartphone 1.

In step S1004, if the current position is near the seashore (YES in S1004), seawater immersion determination unit 4 advances the process to step S1004.

In step S1005, seawater immersion determination unit 4 can determine that smartphone 1 has been immersed in seawater, and can increment the value of the determination counter.

In step S1006, if the value of the determination counter is more than or equal to threshold value TH1 (YES in S1006), the process proceeds into step S1007, and if the value of the determination counter is less than threshold value TH1 (NO in S1006), the process proceeds into step S1009.

In step S1008, water-washing necessity determination unit 15 can determine that smartphone 1 should be washed in water, and can set the current mode into the warning mode.

In step S1009, if smartphone 1 is powered off (YES in S1009), the process proceeds into step S1010, and if smartphone 1 is left powered on (NO in S1009), the process proceeds into step S1011.

In step S1010, seawater immersion determination unit 4 causes memory 8 to store the value of the determination counter.

After the process waits a certain time period in step S1011, the process is returned to step S202.

As described above, this variation notifies a warning to wash smartphone 1 in water if it is determined that the number of times of immersion in seawater is more than or equal to a threshold value based on the current position of smartphone 1 and based on whether or not smartphone 1 has been immersed in water. Thus, it is particularly effective in such a case where accumulated salt crystals increase as the number of times that smartphone 1 has been immersed in seawater is larger.

Sixth Embodiment

Figure 21:
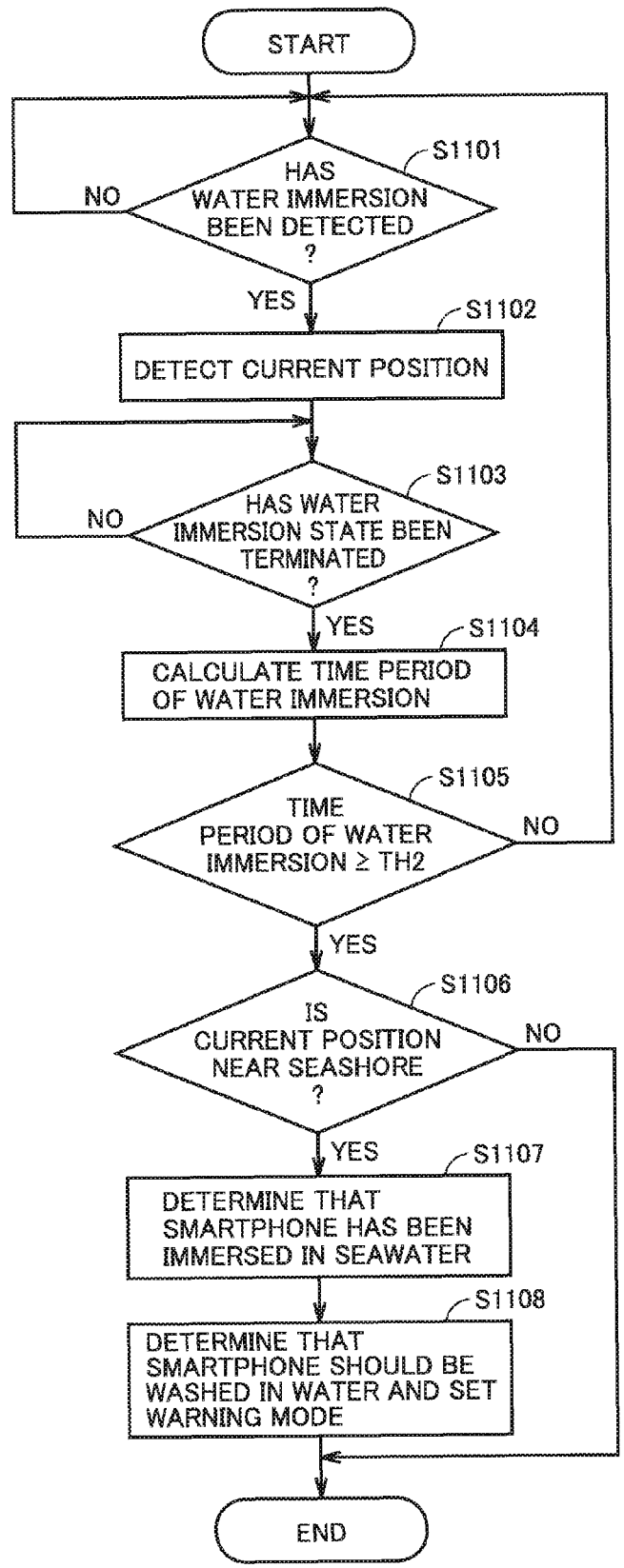
FIG. 21 is a flowchart representing a procedure of determining whether or not a smartphone should be washed in water according to a sixth embodiment.

FIG. 21 is a flowchart representing a procedure of determining whether or not smartphone 1 should be washed in water according to a sixth embodiment.

In step S1101, if water immersion detection unit 51 detects that smartphone 1 has been immersed in water (YES in S1101), the process proceeds into step S1102.

In step S1102, position detection unit 43 can detect the current position of smartphone 1.

In step S1103, if water immersion detection unit 51 detects that water immersion of smartphone 1 has been terminated (YES in S1103), the process proceeds into step S1104.

In step S1104, seawater immersion determination unit 4 can calculate the time period in which smartphone 1 has been immersed in water.

In step S1105, if the time period in which smartphone 1 has been immersed in water is more than or equal to predetermined value TH2 (YES in S1105), the process proceeds into step S1106.

In step S1106, if the current position is near the seashore (YES in S1106), seawater immersion determination unit 4 advances the process to step S1107.

In step S1107, seawater immersion determination unit 4 can determine that smartphone 1 has been immersed in seawater.

In step S1108, water-washing necessity determination unit 15 can determine that smartphone 1 should be washed in water, and can set the current mode into the warning mode.

As described above, the sixth embodiment does not determine that smartphone 1 has been immersed in seawater if the time period of water immersion is more than or equal to the threshold value. Thus, it is particularly effective in such a case where salt crystals are less likely to be left after drying smartphone 1 having been immersed in seawater for only a short while.

Variation of Sixth Embodiment

Figure 22:
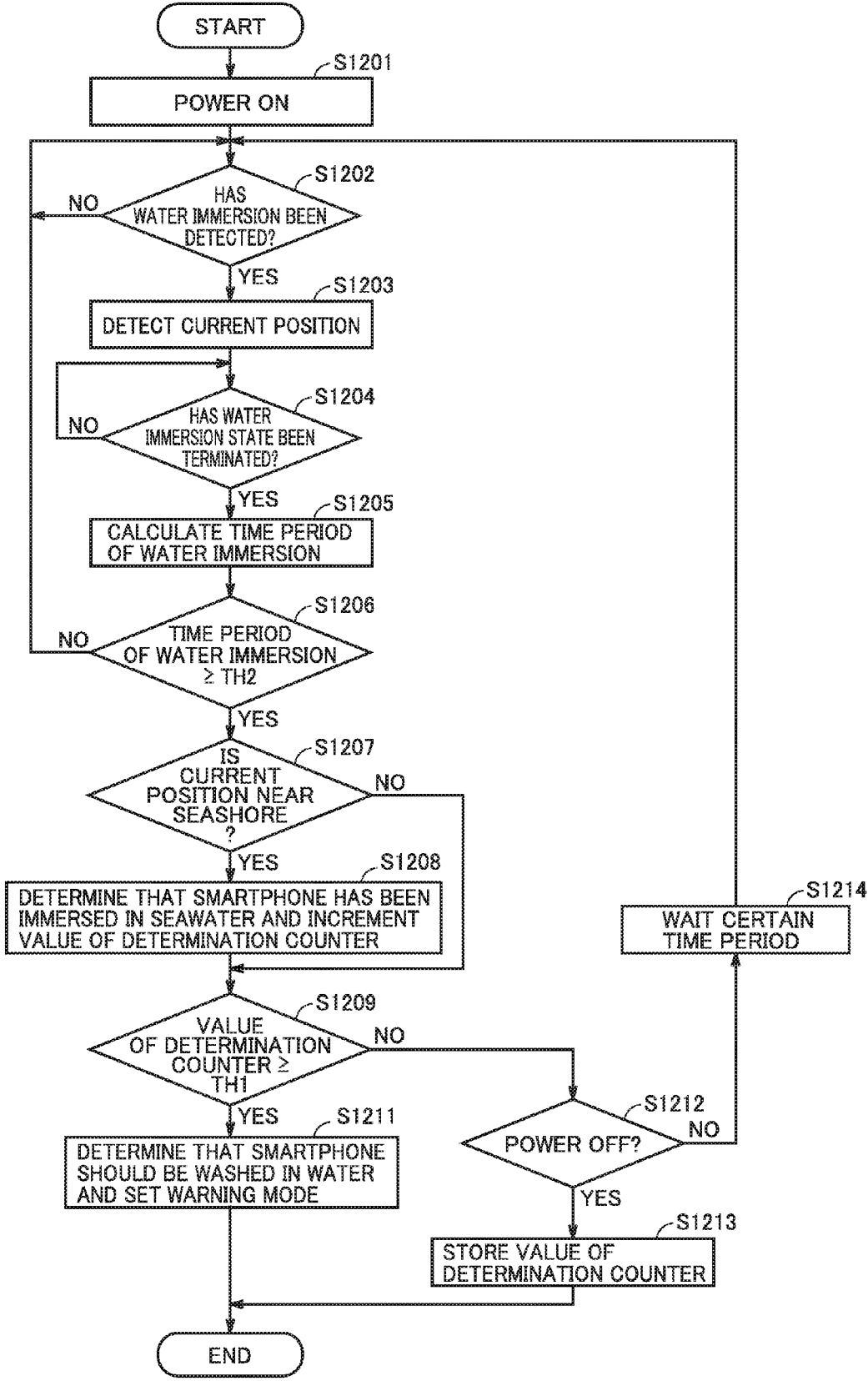
FIG. 22 is a flowchart representing a procedure of determining whether or not a smartphone should be washed in water according to a variation of the sixth embodiment.

FIG. 22 is a flowchart representing a procedure of determining whether or not smartphone 1 should be washed in water according to a variation of the sixth embodiment.

In step S1201, smartphone 1 is powered on.

In step S1202, if water immersion detection unit 51 detects that smartphone 1 has been immersed in water (YES in S1201), the process proceeds into step S1202.

In step S1203, position detection unit 43 can detect the current position of smartphone 1.

In step S1204, if water immersion detection unit 51 detects that water immersion of smartphone 1 has been terminated (YES in S1204), the process proceeds into step S1205.

In step S1205, seawater immersion determination unit 4 can calculate the time period in which smartphone 1 has been immersed in water.

In step S1206, if the time period in which smartphone 1 has been immersed in water is more than or equal to predetermined value TH2 (YES in S1206), the process proceeds into step S1207.

In step S1207, if the current position is near the seashore (YES in S1207), seawater immersion determination unit 4 advances the process to step S1208.

In step S1208, seawater immersion determination unit 4 can determine that smartphone 1 has been immersed in seawater, and can increment the value of the determination counter.

In step S1209, if the value of the determination counter is more than or equal to threshold value TH1 (YES in S1209), the process proceeds into step S1210, and if the value of the determination counter is less than threshold value TH1 (NO in S1209), the process proceeds into step S1212.

In step S1211, water-washing necessity determination unit 15 can determine that smartphone 1 should be washed in water, and can set the current mode into the warning mode.

In step S1212, if smartphone 1 is powered off (YES in S1212), the process proceeds into step S1213, and if smartphone 1 is left powered on (NO in S1212), the process proceeds into step S1214.

In step S1213, seawater immersion determination unit 4 causes memory 8 to store the value of the determination counter.

After the process waits a certain time period in step S1214, the process is returned to step S202.

As described above, this variation notifies a warning to wash smartphone 1 in water if it is determined that the number of times of immersion in seawater is more than or equal to a threshold value based on the current position of smartphone 1 and the time period in which smartphone 1 has been immersed in water. Thus, it is particularly effective in such a case where accumulated salt crystals increase as the number of times that smartphone 1 has been immersed in seawater is larger.

(Variations)

The present disclosure is not limited to the above-described embodiments, but also includes variations as will be described below, for example.

(1) Detection of Water Washing

The second and third embodiments detect that water washing has been performed in the case where the smartphone has been immersed in water having a salt concentration of less than or equal to a predetermined value, but this is not a limitation. Since salt crystals, when immersed in high-temperature water, characteristically tend to be dissolved in water, this property may be utilized. For example, the water washing detection unit may include a temperature sensor to detect that water washing has been performed if the smartphone has been immersed in water having a temperature of more than or equal to a predetermined temperature.

(2) Residual Amount of Salt Crystals

The smartphone may be configured to estimate the residual amount of salt crystals after drying based on the concentration of seawater in which the smartphone has been immersed, the time period of immersion in seawater, and the number of times of immersion in seawater. The smartphone may be configured to estimate the removed amount of salt crystals based on the time period of water washing.

(3) Weighted Count

The first to third embodiments count the number of times of immersion in salt water having a salt concentration of more than or equal to a predetermined value, but this is not a limitation. Weighted count with a larger weight as the salt concentration is higher or weighted count with a larger weight as the time period of immersion is longer may be performed.

(4) Warning Notice

In the above-described embodiments, a warning is provided by a pop-up display or displayed by an icon, but this is not a limitation. For example, a warning may be notified by an audio message, or an audible alert may be provided.

The above-described embodiments provide a pop-up display of a warning immediately after the smartphone is powered on or after the smartphone is unlocked, and otherwise, display a warning icon, but this is not a limitation. For example, a pop-up display of a warning may be provided at regular time intervals.

(5) Detection of Water Immersion

In the above-described embodiments, the water immersion detection unit detects water immersion of the smartphone by detecting the capacitance of the capacitance touch panel, but this is not a limitation. For example, water immersion may be detected by using an air pressure sensor to measure the air pressure. Alternatively, water immersion of the smartphone may be detected by detecting the pressure imposed on a pressure-sensitive type touch panel. Specifically, the water immersion detection unit detects that the smartphone has been immersed in water when the pressure becomes more than or equal to a predetermined value THX and less than threshold value TH1 in the entire region of the pressure-sensitive type touch panel. Threshold value TH1 is a threshold value for detecting that a user has touched the touch panel with his/her finger.

(6) Determination on Seawater Immersion

The fourth and fifth embodiments determine that smartphone 1 has been immersed in seawater based on whether the smartphone is located near the seashore, but this is not a limitation. For example, an acceleration sensor may be used to detect falling of the smartphone. The seawater immersion determination unit may determine that the smartphone has been immersed in seawater when the smartphone is located near the seashore and when falling of the smartphone has been detected.

(7) Location Near Seashore and Determination on Seawater Immersion of Smartphone In the fourth embodiment and the variation thereof, the seawater immersion determination unit immediately determines that the smartphone has been immersed in seawater when it is detected that the current position of the smartphone is near the seashore. The seawater immersion determination unit determines that the smartphone has been immersed in seawater if it is YES in step S702 shown in FIG. 16 and if it is YES in step S803 shown in FIG. 17. However, the present disclosure is not limited thereto.

The seawater immersion determination unit may determine that the smartphone has been immersed in seawater if the state where the current position of the smartphone is near the seashore continues for a predetermined time period. The seawater immersion determination unit may advance the process to step S703 and S804 when the state where the current position of the smartphone is near the seashore continues for the predetermined time period after YES in step S702 shown in FIG. 16 and step S803 shown in FIG. 17, and when the state does not continue for the predetermined time period, returns the process to step S701 and S801.

Although the present disclosure has been described and illustrated in detail, it is clearly understood that the same is by way of illustration and example only and is not to be taken by way of limitation, the scope of the present disclosure being interpreted by the terms of the appended claims.

The invention claimed is:

1. An electronic device comprising:
   a display;
   a water immersion detection unit configured to detect that the electronic device has been immersed in water;
   a salt detection unit configured to measure a salt concentration if it is detected that the electronic device has been immersed in water; and
   a processor configured to make a determination whether or not the electronic device has been immersed in seawater based on the salt concentration, to determine whether or not the electronic device should be washed in water based on a result of the determination, and if it is determined that the electronic device should be washed in water, to cause the display to display a warning.

2. The electronic device according to claim 1, wherein the processor is configured to determine that the electronic device has been immersed in seawater if the salt concentration is more than or equal to a first predetermined value.

3. The electronic device according to claim 1, wherein the processor is configured to increment a value of a determination counter if the salt concentration is more than or equal to a first predetermined value, and to determine that the electronic device should be washed in water when the value of the determination counter is more than or equal to a threshold value.

4. The electronic device according to claim 1, wherein the processor is configured to determine whether or not the electronic device has been immersed in seawater based on the salt concentration if a time period in which the electronic device has been immersed in water is longer than or equal to a first predetermined time period.

5. The electronic device according to claim 1, wherein the processor is configured to increment a value of a determination counter if a time period in which the electronic device has been immersed in water is longer than or equal to a first predetermined time period and if the salt concentration when it is detected that the electronic device has been immersed in water is more than or equal to a first predetermined value, and to determine that the electronic device should be washed in water when the value of the determination counter is more than or equal to a threshold value.

6. The electronic device according to claim 1, wherein the processor is configured to detect that the electronic device has been washed in water if the water immersion detection unit detects water immersion after the determination that the electronic device has been immersed in seawater and if the salt concentration detected by the salt detection unit is less than or equal to a second predetermined value.

7. The electronic device according to claim 1, wherein the processor is configured to detect that the electronic device has been washed in water if the water immersion detection unit detects that a time period in which the electronic device has been immersed in water is longer than or equal to a second predetermined time period after the determination that the electronic device has been immersed in seawater and if the salt concentration detected by the salt detection unit is less than or equal to a second predetermined value.

8. The electronic device according to claim 7, wherein the processor is configured to delete the warning displayed on the display if it is detected that the electronic device has been washed in water.

9. The electronic device according to claim 8, wherein the processor is further configured to notify that water washing has been detected.

10. The electronic device according to claim 1, wherein the water immersion detection unit includes a touch panel.

11. An electronic device comprising:
    a display;
    a water immersion detection unit configured to detect that the electronic device has been immersed in water;
    a position detection unit configured to detect a current position of the electronic device if it is detected that the electronic device has been immersed in water; and
    a processor configured to make a determination whether or not the electronic device has been immersed in seawater based on the current position, to determine whether or not the electronic device should be washed in water based on a result of the determination, and if it is determined that the electronic device should be washed in water, to cause the display to display a warning.

12. The electronic device according to claim 11, wherein the processor is configured to determine that the electronic device has been immersed in seawater if the current position is near a seashore.

13. The electronic device according to claim 11, wherein the processor is configured to increment a value of a determination counter if the current position is near a seashore when it is detected that the electronic device has been immersed in water, and to determine that the electronic device should be washed in water when the value of the determination counter is more than or equal to a threshold value.

14. The electronic device according to claim 11, wherein the processor is configured to determine that the electronic device has been immersed in seawater if a time period in which the electronic device has been immersed in water is longer than or equal to a first predetermined time period and if the current position is near a seashore.

15. The electronic device according to claim 11, wherein the processor is configured to increment a value of a determination counter if a time period in which the electronic device has been immersed in water is longer than or equal to a first predetermined time period and if the current position is near a seashore, and to determine that the electronic device should be washed in water when the value of the determination counter is more than or equal to a threshold value.

* * * * *